(12) United States Patent
Sakuma et al.

(10) Patent No.: US 9,248,103 B2
(45) Date of Patent: Feb. 2, 2016

(54) METHOD FOR IMPROVING WATER SOLUBILITY OF SLIGHTLY SOLUBLE SUBSTANCE

(71) Applicant: Kabushiki Kaisha Sangi, Tokyo (JP)

(72) Inventors: Shuji Sakuma, Tokyo (JP); Keiichiro Kikukawa, Tokyo (JP); Ryosuke Miyasaka, Tokyo (JP)

(73) Assignee: KABUSHIKI KAISHA SANGI, Tokyo (JP)

( * ) Notice: Subject to any disclaimer, the term of this patent is extended or adjusted under 35 U.S.C. 154(b) by 0 days.

(21) Appl. No.: 14/380,442

(22) PCT Filed: Feb. 21, 2013

(86) PCT No.: PCT/JP2013/001000
§ 371 (c)(1),
(2) Date: Aug. 22, 2014

(87) PCT Pub. No.: WO2013/128858
PCT Pub. Date: Sep. 6, 2013

(65) Prior Publication Data
US 2015/0010638 A1 Jan. 8, 2015

(30) Foreign Application Priority Data

Mar. 2, 2012 (JP) ................................. 2012-047399

(51) Int. Cl.
| | |
|---|---|
| A61K 9/50 | (2006.01) |
| A01N 25/26 | (2006.01) |
| A61K 8/24 | (2006.01) |
| A61K 8/19 | (2006.01) |
| A23L 1/03 | (2006.01) |
| A61K 9/16 | (2006.01) |
| A61K 8/02 | (2006.01) |
| A61K 31/10 | (2006.01) |
| A61K 31/167 | (2006.01) |
| A61K 31/18 | (2006.01) |
| A61K 31/195 | (2006.01) |
| A61K 31/40 | (2006.01) |
| A61K 31/426 | (2006.01) |
| A61K 31/4515 | (2006.01) |
| A61K 31/505 | (2006.01) |
| A61K 31/7048 | (2006.01) |
| B05D 3/12 | (2006.01) |
| B05D 5/04 | (2006.01) |
| A61K 8/44 | (2006.01) |
| A61K 8/46 | (2006.01) |
| A61K 8/67 | (2006.01) |
| A61Q 19/00 | (2006.01) |
| A01N 25/00 | (2006.01) |
| A61K 9/14 | (2006.01) |

(52) U.S. Cl.
CPC ................ *A61K 9/501* (2013.01); *A01N 25/00* (2013.01); *A01N 25/26* (2013.01); *A23L 1/0305* (2013.01); *A61K 8/0241* (2013.01); *A61K 8/19* (2013.01); *A61K 8/24* (2013.01); *A61K 8/44* (2013.01); *A61K 8/463* (2013.01); *A61K 8/676* (2013.01); *A61K 9/143* (2013.01); *A61K 9/1611* (2013.01); *A61K 31/10* (2013.01); *A61K 31/167* (2013.01); *A61K 31/18* (2013.01); *A61K 31/195* (2013.01); *A61K 31/40* (2013.01); *A61K 31/426* (2013.01); *A61K 31/4515* (2013.01); *A61K 31/505* (2013.01); *A61K 31/7048* (2013.01); *A61Q 19/00* (2013.01); *B05D 3/12* (2013.01); *B05D 5/04* (2013.01); *A23V 2002/00* (2013.01); *A61K 9/5089* (2013.01); *A61K 2800/412* (2013.01); *A61K 2800/413* (2013.01); *A61K 2800/49* (2013.01)

(58) Field of Classification Search
None
See application file for complete search history.

(56) References Cited

U.S. PATENT DOCUMENTS

| | | | |
|---|---|---|---|
| 3,966,899 A | 6/1976 | Nakai et al. | |
| 4,859,471 A | 8/1989 | Fulberth et al. | |
| 5,122,418 A | 6/1992 | Nakane et al. | |
| 9,023,398 B2 * | 5/2015 | Sakuma et al. | ........ A01N 25/08 424/490 |
| 2003/0162287 A1 | 8/2003 | Yamamoto et al. | |
| 2006/0153913 A1 | 7/2006 | Yamane et al. | |
| 2007/0243260 A1 | 10/2007 | Snape et al. | |
| 2012/0264608 A1* | 10/2012 | Sakuma et al. | ............... 504/358 |

FOREIGN PATENT DOCUMENTS

| | | |
|---|---|---|
| EP | 1072650 | 1/2001 |
| EP | 2 338 480 A1 | 6/2011 |

(Continued)

OTHER PUBLICATIONS

L Jongpaiboonkit, T Franklin-Ford, WL Murphy. "Growth of Hydroxyapatite Coatings on Biodegradable Polymer Microspheres." Applied Materials & Interfaces, vol. 1 No. 7, 2009, pp. 1504-1511.*

(Continued)

*Primary Examiner* — Isaac Shomer
(74) *Attorney, Agent, or Firm* — Kenneth H. Sonnenfeld; Margaret B. Brivanlou; King & Spalding LLP

(57) ABSTRACT

It is an object of the present invention to provide a method for improving the solubility of a poorly-soluble substance, which is capable of increasing the solubility of substantially all poorly-soluble substances. This is a method comprising coating the surface of a poorly-soluble substance particle with microparticles of a calcium compound such as calcium phosphate or calcium carbonate, and at least one selected from a pH adjuster and a surfactant, by applying mechanical energy thereto.

14 Claims, No Drawings

(56) References Cited

FOREIGN PATENT DOCUMENTS

| | | |
|---|---|---|
| JP | 51-32719 | 3/1976 |
| JP | 61-145124 | 7/1986 |
| JP | 04-308513 | 10/1992 |
| JP | 05-032524 | 2/1993 |
| JP | 05-178765 | 7/1993 |
| JP | 05-271066 | 10/1993 |
| JP | 07-304633 | 11/1995 |
| JP | 07-328416 | 12/1995 |
| JP | 08-301763 | 11/1996 |
| JP | 2642486 | 5/1997 |
| JP | 10-025255 | 1/1998 |
| JP | 2000-095655 | 4/2000 |
| JP | 2001-098185 | 4/2001 |
| JP | 2002-519316 | 7/2002 |
| JP | 2003-104911 | 4/2003 |
| JP | 2006-016392 | 1/2006 |
| JP | 2006-131709 | 5/2006 |
| JP | 2007-176869 | 7/2007 |
| JP | 2007-536362 | 12/2007 |
| JP | 2008-007479 | 1/2008 |
| JP | 2008-120757 | 5/2008 |
| WO | WO 97/06781 | 2/1997 |
| WO | WO 00/00177 | 1/2000 |
| WO | WO 2005/018607 | 3/2005 |
| WO | WO 2005/037268 | 4/2005 |
| WO | WO 2008149096 A2 * | 12/2008 |
| WO | WO 2010/121327 | 10/2010 |
| WO | WO 2010/121328 | 10/2010 |
| WO | WO 2011/039952 | 4/2011 |
| WO | WO 2011039952 A1 * | 4/2011 |
| WO | WO 2012071014 A1 * | 5/2012 |

OTHER PUBLICATIONS

Bermudez et al., Pulmonary Responses of Mice, Rats, and Hamsters to Subchronic Inhalation of Ultrafine Titanium Dioxide Particles, 2004, Toxicological Sciences, vol. 77, No. 2, pp. 347-357.

Kohsaku Kawakami, "Importance of Surface Chemistry in the Development of Pharmaceutical Products," *Division of Colloid and Surface Chemistry, The 23$^{rd}$ Modern Colloid and Surface Chemistry Basic Course*, May 16-18, 2007, 17 pages.

Kabushiki Kaisha Sangi, International Search Report for PCT/JP2010/005545, dated Oct. 19, 2010, 8 pages.

Kabushiki Kaisha Sangi JP, Inquiry of Substantive Examination for Russian Patent Application No. 2012115189/15 dated May 21, 2013, 7 pages.

Total Polystyrene Material Safety Data Sheet, 2009, Total Petro Chemicals, USA, Inc., pp. 1-6.

English machine translation dated Aug. 11, 2013 of Noguchi et al., (JP 2001-98185, published Apr. 10, 2001), pp. 1-6.

English machine translation dated Apr. 4, 2014 of Uchiyama et al, JP 2000095655, published Apr. 4, 2000.

Occupational Health Guideline for Mica, Sep. 1978, U.S. Dept. of Health and Human Services and U.S. Dept. of Labor, pp. 1-4.

Extended European Search Report for corresponding application EP13754690.9, mailed Jul. 29, 2015 (7 pages).

* cited by examiner

METHOD FOR IMPROVING WATER SOLUBILITY OF SLIGHTLY SOLUBLE SUBSTANCE

TECHNICAL FIELD

The present invention relates to a method for improving the aqueous solubility of a poorly-soluble substance used in pharmaceutical products, veterinary pharmaceutical products, quasi-drugs, cosmetic products, food products, agricultural chemicals, and the like.

BACKGROUND ART

Useful substances have often poor solubility in water in the fields of pharmaceutical products, veterinary pharmaceutical products, quasi-drugs, cosmetic products, food products, agricultural chemicals, and the like. This restricts the use of useful substances. Thus, it has been desired to develop a method for improving the solubility of poorly-soluble useful substances.

Under such circumstances, the present inventors had proposed a method for improving the solubility of a poorly-soluble substance, wherein the surface of the poorly-soluble substance particle is coated by applying mechanical energy to allow the microparticles of a calcium compound such as calcium phosphate or calcium carbonate to penetrate into the poorly-soluble substance particle to improve the solubility (see Patent Document 1).

PRIOR ART DOCUMENTS

Patent Documents

Patent Document 1: WO2011/039952

SUMMARY OF THE INVENTION

Object to be Solved by the Invention

The above described method for improving the solubility of a poorly-soluble substance by coating the surface of the poorly-soluble substance particle with the microparticles of a calcium compound such as calcium phosphate or calcium carbonate can be an extremely useful means for increasing the solubility of poorly-soluble substances. However, there has been a case in which the desired solubility cannot necessarily be obtained, depending on the type of a poorly-soluble substance.

It is an object of the present invention to provide a method for improving the solubility of a poorly-soluble substance, which is capable of increasing the solubility of substantially all poorly-soluble substances.

Means to Solve the Object

With regard to the aforementioned method proposed by the present inventors, the inventors have searched for various additives and have further studied regarding modification of the particles of poorly-soluble substances, etc. As a result, the inventors have found that the dispersibility of a poorly-soluble substance can be improved by coating the surface of the poorly-soluble substance particle with microparticles of a calcium compound such as calcium phosphate or calcium carbonate, and particularly hydroxyapatite, and also with a pH adjuster and/or a surfactant, by applying mechanical energy thereto, and thus that the solubility of the poorly-soluble substance can be improved.

In the case of a method using calcium compound microparticles, it is assumed that as soon as a poorly-soluble substance coated with the calcium compound microparticles is contacted with water, a part of crystals of the poorly-soluble substance would be removed together with the calcium compound microparticles, and the surface area of the poorly-soluble substance would be thereby increased, and also that small calcium compound microparticles, as well as the poorly-soluble substance, would be in a state in which they are nearly dissolved in water, and the amount of the poorly-soluble substance dissolved would be thereby improved. Accordingly, it is considered that, by coating the surface of a poorly-soluble substance particle with calcium compound microparticles and also with a pH adjuster and/or a surfactant according to a method comprising applying mechanical energy thereto, the force of allowing the calcium compound microparticles to compressively adhere to the surface of the poorly-soluble substance can be increased, and when the calcium compound microparticles are removed from the poorly-soluble substance, its removing action or dispersing action can be maximized.

Specifically, the present invention relates to:
(1) a method for producing a substance with improved aqueous solubility, comprising coating the surface of a poorly-soluble substance particle with calcium compound microparticles and at least one selected from a pH adjuster and a surfactant by applying mechanical energy, to produce the substance with improved aqueous solubility;
(2) the method for producing a substance with improved aqueous solubility according to (1) above, wherein the calcium compound is calcium phosphate or calcium carbonate;
(3) the method for producing a substance with improved aqueous solubility according to (2) above, wherein the calcium phosphate is hydroxyapatite or tricalcium phosphate;
(4) the method for producing a substance with improved aqueous solubility according to any one of (1) to (3) above, wherein at least 5% of the surface of the poorly-soluble substance particle is coated with the calcium compound microparticles;
(5) the method for producing a substance with improved aqueous solubility according to any one of (1) to (4) above, which is a method using at least a pH adjuster, wherein the pH adjuster is used so that the pH of an aqueous solution of the substance with improved aqueous solubility becomes pH 6 or more;
(6) the method for producing a substance with improved aqueous solubility according to any one of (1) to (4) above, which is a method using at least a surfactant, wherein the amount of the surfactant used is 1% to 300% by mass with respect to the poorly-soluble substance;
(7) the method for producing a substance with improved aqueous solubility according to any one of (1) to (6) above, wherein the method of applying mechanical energy is a method involving mechanical fusion;
(8) the method for producing a substance with improved aqueous solubility according to any one of (1) to (6) above, wherein the method of applying mechanical energy is a method involving hybridization;
(9) the method for producing a substance with improved aqueous solubility according to any one of (1) to (8) above, wherein the mean particle diameter of the calcium compound microparticles is 100 μm or less;

(10) the method for producing a substance with improved aqueous solubility according to (9) above, wherein the mean particle diameter of the calcium compound microparticles is 50 to 200 nm;

(11) the method for producing a substance with improved aqueous solubility according to any one of (1) to (5) and (7) to (10) above, wherein the pH adjuster is at least one selected from the group consisting of disodium hydrogen phosphate, L-arginine, sodium hydrogen carbonate, citric acid, and sodium dihydrogen phosphate;

(12) the method for producing a substance with improved aqueous solubility according to any one of (1) to (4) and (6) to (10) above, wherein the surfactant is sodium dodecyl sulfate; and

(13) the method for producing a substance with improved aqueous solubility according to any one of (1) to (12) above, wherein the poorly-soluble substance is a substance acting as an active ingredient of any one of a pharmaceutical product, a veterinary pharmaceutical product, a quasi-drug, a cosmetic product and an agricultural chemical, or a food additive.

Furthermore, the present invention relates to:

(14) a substance with improved aqueous solubility obtained by the method according to any one of (1) to (13) above;

(15) a pharmaceutical product, a veterinary pharmaceutical product, a quasi-drug, a cosmetic product, an agricultural chemical or a food product, comprising the substance with improved aqueous solubility according to (14) above; and

(16) the pharmaceutical product, veterinary pharmaceutical product, quasi-drug, cosmetic product, agricultural chemical or food product according to (15) above, which is an aqueous liquid composition.

Effect of the Invention

According to the present invention, the solubility of all poorly-soluble substances, which are used for pharmaceutical products, veterinary pharmaceutical products, quasi-drugs, cosmetic products, food products, agricultural chemicals, and the like, can be increased. In addition, the present invention is advantageous in terms of productivity and cost performance, it is excellent in terms of safety for workers, and it is highly useful in industrial application.

MODE OF CARRYING OUT THE INVENTION

The method for producing a substance with improved aqueous solubility of the present invention is not particularly limited, as long as it is a method which comprises coating the surface of a poorly-soluble substance particle with calcium compound microparticles and at least one selected from a pH adjuster and a surfactant by applying mechanical energy thereto. The term "dissolution" is used in the present invention to not only include a state in which a substance is completely dissolved in water, but also include a state in which a substance is uniformly dispersed in an aqueous medium and it seems a transparent liquid by visual observation, such as a solubilized state as a result of micelle formation or the like. It means a state in which the amount of a substance dissolved can be measured by a test method generally used in the measurement of the dissolved amount of such a substance.

In the present invention, the surface of a poorly-soluble substance particle is coated with calcium compound microparticles and also with a pH adjuster and/or surfactant according to a method of applying mechanical energy thereto. Accordingly, it is considered that the force of allowing the calcium compound microparticles to compressively adhere to the surface of the poorly-soluble substance can be increased, and when the calcium compound microparticles are removed from the poorly-soluble substance, its removing action or dispersing action can be maximized.

Moreover, in the case of a poorly-soluble substance exhibiting acidity, since calcium compound microparticles are dissolved in acid, the calcium compound microparticles need to exhibit their dispersion force without being completely dissolved, with respect to a decrease in pH occurring upon the dissolution of the poorly-soluble substance. Furthermore, the solubility of a weak electrolyte such as a poorly-soluble substance is changed depending on the pH of a solution. Thus, the higher the pH of a weakly acidic compound, the larger the ratio of an ionic form that can be obtained, and as a result, solubility increases. Accordingly, in the case of a poorly-soluble substance exhibiting acidity, it is considered that the pH is increased by addition of a pH adjuster, so that synergic effects between the improvement of dissolution by the calcium compound microparticles and the improvement of the solubility of the poorly-soluble substance itself can be exhibited. Further, in the case of a poorly-soluble substance exhibiting basicity, it is considered that the solubility of a poorly-soluble substance is suppressed because the pH of the coating calcium compound microparticles is basic. In this case, the pH of a local portion that is contacted with the poorly-soluble substance is more important than the pH of a solution as a whole, and it is considered that the effect of improving aqueous solubility can be further increased by decreasing the pH of a solution contacted with the poorly-soluble substance by addition of a pH adjuster. Still further, it is considered that a surfactant is capable of improving the dispersibility of a poorly-soluble substance in water and of promoting solubilization.

In the method of the present invention in which a pH adjuster is used, with respect to a poorly-soluble substance exhibiting acidity (calcium-coated poorly-soluble substance), a pH adjuster exhibiting stronger basicity can be used, and with respect to a poorly-soluble substance exhibiting basicity (calcium-coated poorly-soluble substance), a pH adjuster exhibiting stronger acidity can be used. It is preferable to use a pH adjuster such that the pH of an aqueous solution of a substance with improved aqueous solubility becomes pH 6 or more. That is to say, with respect to an acidic poorly-soluble substance having a low pH value, it is preferable to add a pH adjuster to a solution such that the pH of an aqueous solution of the substance with improved aqueous solubility becomes at least pH 6. On the other hand, with respect to a basic poorly-soluble substance as well, it is preferable to add a pH adjuster to a solution such that pH of an aqueous solution of the substance with improved aqueous solubility does not become extremely low and that it becomes pH 6 or more. A mechanism of further improving solubility by retaining pH 6 or more has not necessarily been elucidated. It is assumed that if pH is less than 6, the dissolution of a calcium compound would progress and it would affect the removing action or dispersing action upon the removal of the calcium compound from a poorly aqueous soluble substance.

Moreover, as described above, since the pH of a local portion that is contacted with a poorly-soluble substance is more important than the pH of a solution as a whole, when an acidic substance is dissolved, desired effects can be obtained even though the pH is not extremely high. It is sufficient if a pH adjuster is used such that the pH of an aqueous solution of a substance with improved aqueous solubility becomes pH 8 or less. Accordingly, it is preferable to use a pH adjuster such that the pH of an aqueous solution of a substance with improved aqueous solubility becomes pH 6 to 8. Herein, the pH of an aqueous solution indicates a pH value that is measured 60 minutes after the addition of a target substance to 50 mL of distilled water in an amount 2 times larger than the substance dissolved in 360 minutes. More specifically, the pH of an aqueous solution indicates a pH value that is measured according to [Dissolution test of poorly-soluble substances] in the below-mentioned Examples.

The method of the present invention in which a pH adjuster is used is effective for poorly-soluble substances having any pH value. The present method is more effective in the case of using a poorly-soluble substance, regarding which the pH of an aqueous solution containing the calcium-coated substance is less than 6 or more than 8. The present method is particularly effective in the case of using a poorly-soluble substance, regarding which the pH of an aqueous solution containing the calcium-coated substance is less than 5 or more than 9.

In addition, in the method of the present invention in which a surfactant is used, the surfactant is used at a percentage of preferably 1% to 300% by mass, and more preferably 10% to 200% by mass, based on the total mass of a poorly-soluble substance. As the amount of such a surfactant added increases, the effect of improving dissolution becomes higher. However, taking into consideration toxicity and the like, the surfactant is used in an amount used in common practice.

Moreover, in the present invention, it is preferable to use a pH adjuster in combination with a surfactant. Since the effect of improving a dissolved amount by a pH adjuster is different from the effect of improving a dissolved amount by a surfactant in terms of action, the effect of improving solubility can be enhanced by each action.

Specific examples of the coating method of the present invention include: a method which comprises coating the surface of a poorly-soluble substance particle with calcium compound microparticles by applying mechanical energy thereto, and then coating the aforementioned surface with a pH adjuster and/or a surfactant by applying mechanical energy thereto (method A); a method which comprises coating the surface of a poorly-soluble substance particle with a pH adjuster and/or a surfactant by applying mechanical energy thereto, and then coating the aforementioned surface with calcium compound microparticles by applying mechanical energy thereto (method B); and a method which comprises coating the surface of a poorly-soluble substance particle with a mixture of calcium compound microparticles and a pH adjuster and/or a surfactant by applying mechanical energy thereto (method C). In the present invention, since the particle of a poorly-soluble substance is coated by applying mechanical energy, a part or the entire of calcium compound microparticles, a pH adjuster, and a surfactant is allowed to penetrate into the poorly-soluble substance particle, and thereby, the surface of the poorly-soluble substance particle can be coated. In the case of the above described method A and method B, there is a case in which a substance as a second layer would not reach the particle of the poorly-soluble substance and it would penetrate into a first layer. In the present invention, in order to obtain higher solubility, it is particularly preferable to adopt a method which comprises coating the surface of a poorly-soluble substance particle with a mixture of calcium compound microparticles and a pH adjuster and/or a surfactant by applying mechanical energy thereto (method C).

The calcium compound is preferably a poorly-soluble calcium compound that is hardly dissolved in water. Examples of such a compound include calcium phosphate, calcium carbonate, calcium sulfate, and calcium hydroxide. Of these, calcium phosphate and calcium carbonate are preferable. These calcium compounds may be used singly or in the form of a mixture of two or more types.

An example of the calcium phosphate is a calcium phosphate having a Ca/P ratio of 0.8 to 2.0, and preferably having a Ca/P ratio of 1.0 to 2.0. Specific examples of such calcium phosphate include hydroxyapatite, tricalcium phosphate, tetracalcium phosphate, octacalcium phosphate, calcium hydrogen phosphate, calcium pyrophosphate, and calcium metaphosphate. Of these, hydroxyapatite and tricalcium phosphate are preferable. Moreover, the calcium phosphate may be obtained from the nature, or may also be synthesized by a known method such as a wet method or a dry method.

The hydroxyapatite is one type of calcium phosphate, which is a main ingredient of the bone. In general, it is shown as a stoichiometric composition represented by $Ca_{10}(PO_4)_6(OH)_2$. The hydroxyapatite is characterized in that it can exhibit properties as hydroxyapatite and can adopt an apatite structure even if it is a non-stoichiometric composition whose Ca/P molar ratio is not 1.67. In the present invention, both hydroxyapatite as a stoichiometric composition and hydroxyapatite as a non-stoichiometric composition can be used. Hydroxyapatite having a Ca/P molar ratio of 1.4 to 1.8 is preferably used.

In general, as methods for synthesizing hydroxyapatite, there are various types of synthetic methods such as dry synthesis and wet synthesis. In the case of the wet synthesis for example, hydroxyapatite can be obtained by allowing a calcium salt to react with phosphate in an aqueous solution. The Ca/P molar ratio of hydroxyapatite can be controlled by regulating the mixing ratio of a salt as a raw material or synthetic conditions. In the wet synthetic method for example, if an aqueous solution is adjusted to be basic using an ammonia water or the like during the synthesis, the Ca/P molar ratio can be controlled to be high. On the other hand, if the aqueous solution is adjusted to be neutral or weakly acidic using dilute acid, the Ca/P molar ratio can be controlled to be low.

The tricalcium phosphate may be either $\alpha$-$Ca_3(PO_4)_2$ or $\beta$-$Ca_3(PO_4)_2$. Of these, $\alpha$-$Ca_3(PO_4)_2$ is preferable because this is a more bioactive material. As a method for producing tricalcium phosphate, in general, a calcium source is mixed with a phosphoric acid source at a molar ratio of 3:2, and the mixture is then heated at 1200° C. or higher, so as to obtain an $\alpha$-type tricalcium phosphate. On the other hand, the aforementioned mixture is heated at 1000° C. or lower, so as to obtain $\beta$-type tricalcium phosphate. A specific example of the tricalcium phosphate that can be used herein is the tricalcium phosphate described in the Japanese Standards of Food Additives, which contains 98.0% to 103.0% of tricalcium phosphate [$Ca_3(PO_4)_2$] when it is dried. This tricalcium phosphate described in the Japanese Standards of Food Additives is used as an anticaking agent for instant coffee, powdery milk products, condiments, powdered preparations, and the like, or as a calcium source for various types of food products.

The calcium carbonate may be derived from the natural products such as coral, or may also be derived from synthetic products such as calcium oxide, calcium chloride, calcium peroxide, calcium acetate, etc. There can be used the precipitated calcium carbonate described in the Japanese Pharmacopoeia, such as calcium carbonate containing 98.5% or more of calcium carbonate [$CaCO_3$] when it is dried, or the calcium carbonate described in the Japanese Standards of Food Additives, such as calcium carbonate which contains 98.0% to 102.0% of calcium carbonate [$CaCO_3$] when it is dried. These calcium carbonates are used as agents for improving antacid action in gastroduodenal ulcer or gastritis, calcium fortifiers for various types of food products, and the like.

The type of the pH adjuster is not particularly limited, as long as it is a powdery agent (microparticles). Examples of the pH adjuster that can be used herein include substances used as a stabilizing agent, a stabilizer, a plasticizer, a lubricating agent, a lubricant, a solubilizing agent, a solubilizer, a buffering agent, a sweetener, a base agent, a corrigent, a binder, a suspending agent, a suspender, an antioxidant, a brightener, a coating agent, a sustaining agent, a moisturizer, a moisture controlling agent, a filer, an antifoaming agent, an augmenting agent, an antistatic agent, a flavoring agent, an aromatic, a coloring agent, a sugar-coated agent, an isotonizing agent, a softener, an emulsifier, a foaming agent, a skin protective agent, an excipient, a disperser, a disintegrator, a disintegration aid, a fragrance, a desiccant, an antiseptic, a preservative, a soothing agent, a dissolving agent, a dissolution aid, or a fluidizer. In Japan, those described in Japanese Pharmaceutical Excipients (JPE) are preferable.

Specific examples of the pH adjuster exhibiting acidity include ascorbic acid, L-aspartic acid, aspartame, alginic acid, isocyanuric acid, sodium edetate, zinc chloride, ammonium chloride, magnesium chloride, cysteine hydrochloride, triethanolamine hydrochloride, histidine hydrochloride, meprylcaine hydrochloride, kaoline, casein, fructose, captan, carbazochrome sodium sulfonate hydrate, carboxymethyl starch sodium, carmellose calcium, xanthan gum, xylitol, citric acid, sodium dihydrogen citrate, disodium citrate, glycyrrhizic acid, dipotassium glycyrrhizinate, disodium glycyrrhizinate, calcium glycyrrhizinate hydrate, L-glutamine, L-glutamic acid, croscarmellose sodium, crospovidone, aluminum hydroxychloride, light anhydrous silicic acid-containing hydroxypropyl cellulose, crystalline cellulose, crystalline sodium dihydrogen phosphate, gentisic acid ethanolamide, N-cocoyl-arginine ethyl ester-DL-pyrrolidonecarboxylate, succinic acid, monosodium succinate, copolyvidone, choline phosphate, sodium chondroitin sulfate, potassium dichloroisocyanurate, L-cysteine, tartaric acid, D-tartaric acid, potassium hydrogen tartrate, sucralose, sodium thiomalate, tyloxapol, dextran, corn starch, nicotinamide, lactic acid, aluminum lactate, hydroxypropyl starch, hydroxypropyl cellulose, L-phenylalanine, monosodium fumarate, procaine hydrochloride, powdered cellulose, pectin, boric acid, partially neutralized polyacrylate, polysorbate 20, polysorbate 40, polysorbate 60, macrogol 600, macrogol 1000, macrogol 1500, macrogol 1540, macrogol 6000, macrogol 20000, maltose hydrate, malonic acid, anhydrous citric acid, anhydrous sodium dihydrogen phosphate, methanesulfonic acid, DL-methionine, methyl cellulose, sodium N-lauroyl-L-glutamate, L-lysine monohydrochloride, sodium riboflavine phosphate, zinc sulfate hydrate, aluminum sulfate, potassium aluminum sulfate hydrate, oxyquinoline sulfate, DL-malic acid, potassium dihydrogen phosphate, calcium dihydrogen phosphate, and sodium dihydrogen phosphate monohydrate.

Specific examples of the pH adjuster exhibiting basicity include L-arginine, tetrasodium edetate, carrageenan, sodium carboxymethyl starch, carmellose sodium, dried sodium sulfite, dried sodium carbonate, xanthan gum, disodium 5'-guanylate, calcium citrate, sodium citrate hydrate, trisodium glycyrrhizinate, aluminum magnesium silicate, diatomaceous earth, crystalline cellulose-carmellose sodium, disodium succinate hexahydrate, colloidal hydrous aluminum silicate, sodium acetate hydrate, calcium bromide, DL-sodium tartrate, potassium hydroxide, calcium hydroxide, sodium hydroxide, magnesium hydroxide, sodium hydrogen carbonate, magnesium carbonate, sodium thiosulfate hydrate, sodium desoxycholate, sodium copper chlorophyllin, trometamol, sodium propyl paraoxybenzoate, sodium methyl paraoxybenzoate, potato starch, calcium pantothenate, L-histidine, hydroxyethyl cellulose, hypromellose, tetrasodium pyrophosphate, heparin sodium, bentonite, borax, sodium polyacrylate, anhydrous sodium citrate, anhydrous sodium pyrophosphate, anhydrous sodium monohydrogen phosphate, anhydrous trisodium phosphate, meglumine, lauric acid diethanolamide, disodium 5'-ribonucleotide, sodium monohydrogen phosphate heptahydrate, trisodium phosphate, sodium hydrogen phosphate hydrate (disodium hydrogen phosphate), and dipotassium phosphate.

Moreover, a pH adjuster in a neutral range, which exhibits a buffering action to the neutral range of pH during the dissolution of a drug, can also be used. Specific examples of such a pH adjuster in a neutral range include sodium L-aspartate, ethylene carbonate, calcium disodium edetate, sodium erythorbate, dried magnesium sulfate, xanthan gum, calcium gluconate hydrate, L-arginine L-glutamate, potassium L-glutamate, sodium L-glutamate, L-lysine L-glutamate, dihydroxy aluminum amino acetate, D-sorbitol, sodium thiosulfate hydrate, copper chlorophyll, sugar acid calcium, white sugar, and Veegum Neutral.

The type of the surfactant is not particularly limited, as long as it is a powdery agent (microparticles). In Japan, those described in Japanese Pharmaceutical Excipients (JPE) are preferable. Examples of the surfactant include N-cocoyl-L-arginine ester ester-DL-pyrrolidonecarboxylate, N-cocoyl-N-methylaminoethyl sulfonate sodium, cholesterol, self-emulsifying glyceryl monostearate, sucrose fatty acid ester, polyoxyl 40 stearate, cetanol, cetomacrogol 1000, sodium dodecylbenzenesulfonate, polyoxyethylene cetyl ether, polyoxyethylene (105) polyoxypropylene (5) glycol, polyoxyethylene (160) polyoxypropylene (30) glycol, glyceryl monostearate, sorbitan monostearate, N-coconut oil fatty acid acyl-L-arginine-ethyl DL-pyrrolidonecarboxylate, sodium dodecyl sulfate (SDS), sodium lauryl sulfate, diethanolamide laurate, and sodium lauroyl sarcosinate.

The size of the calcium compound microparticle or the microparticle of a pH adjuster and/or a surfactant, which are used in the present invention, is preferably smaller than the particle diameter of a poorly-soluble substance. In addition, the smaller the particle diameter, the larger the specific surface area, and as a result, the rate of coating the poorly-soluble substance can be enhanced. Thus, the particle diameter is preferably as small as possible. Specifically, the present calcium compound microparticles are, for example, particles having a mean particle diameter of preferably 100 μm or less, more preferably 50 μm or less, further preferably 10 μm or less, and particularly preferably 1 μm or less. The lower limit of the particle diameter is not particularly limited. It is generally approximately 0.05 μm for production reasons. The size of a calcium compound microparticle, or of the microparticle of a pH adjuster and/or a surfactant, to be penetrated into the poorly-soluble substance particle serving as a core, is more preferably ⅕ or less, and further preferably ⅒ or less, with respect to the size of the poorly-soluble substance particle because the state of the penetrated calcium compound microparticle, or of the microparticle of a pH adjuster and/or surfactant, can be stably retained when the microparticle has the aforementioned size.

The method of finely grinding the calcium compound and the like is not particularly limited and include a dry method and a wet method, and a general dry mill or wet mill can be used, for example. For instance, a bead mill, a sand mill, a high-speed impact mill, a high-pressure wet atomizing unit, and the like can be used. Specific examples of the bead mill and sand mill include: Visco Mill manufactured by Aimex Co., Ltd.; Grain Mill manufactured by Asada Iron Works Co., Ltd.; Dyno-Mill manufactured by Sinmaru Enterprises Corp.; Anealler Mill manufactured by Mitsui Kozan K. K.; Sand Mill manufactured by Inoue Manufacturing Co., Ltd.; and Sand Mill manufactured by Kotobuki Engineering & Manufacturing Co., Ltd. An example of the high-speed impact mill is Ultra-High-Pressure Homogenizer manufactured by MIZUHO Industrial CO., LTD. Examples of the high-pressure wet atomizing unit include: Nanomizer manufactured by Yoshida Kikai Co., Ltd.; Atomization Apparatus manufactured by Sugino Machine Ltd.; and Atomization Apparatus manufactured by Microfluidics.

In the present invention, as a method of coating a poorly-soluble substance with such calcium compound microparticles or a pH adjuster and/or a surfactant, a method of applying mechanical energy is applied. This is specifically a method comprising coating a poorly-soluble substance with calcium compound microparticles and the like by applying mechanical energy such as physical compression, shearing force or impact force to allow the microparticles and the like to penetrate into the poorly-soluble substance particle. Examples of this coating method include a mechanical fusion method and a hybridization method. More specific examples of such a coating method include: Mechanofusion System (manufactured by Hosokawa Micron Group), Hybridization System (manufactured by Nara Machinery Co., Ltd.), Theta Composer (manufactured by Tokuju Corp.), KRYPTRON (manufactured by Kawasaki Heavy Industries, Ltd.), Mechanomill (manufactured by Okada Seiko Co., Ltd.), CF Mill (manufactured by Ube Industries, Ltd.), COMPOSI (manufactured by Nippon Coke & Engineering Co., Ltd.), Swing Processor (manufactured by Dalton Co., Ltd.), SFP (manufactured by Powrex Corp.), Cyclomix (manufactured by Hosokawa Micron Group), Nanomech Reactor [Simoloyer] (J. TEC Ltd.), MAIC (Aveka, Inc.), and Rotating fluidized bed coater (RFBC) (International Publication WO2007/010396).

Moreover, with regard to the amounts of calcium compound microparticles that coat the poorly-soluble substance, the surface of the particle of the poorly-soluble substance is coated at a percentage of preferably 5% or more, more preferably 60% or more, further preferably 90% or more, and particularly preferably 100%. Coating with a single layer provides sufficient effects, although the poorly-soluble substance may also be coated with two or more layers.

Furthermore, it is preferable to coat the poorly-soluble substance particle such that the outermost layer thereof is coated with a substance having high water absorbability. For example, when a pH adjuster or a surfactant is not a substance having high water absorbability, the above described method B or method C can be adopted. In the case of adopting the method C, it is preferable that the poorly-soluble substance be coated with calcium compound microparticles serving as an outermost layer.

The type of the poorly-soluble substance used in the present invention is not particularly limited, as long as it is a substance having a property that it is hardly dissolved in water. It is a substance having a solubility (25° C.) of, for example, 10000 ppm or less, 5000 ppm or less, 3000 ppm or less, and 1000 ppm or less. Examples of such a poorly-soluble substance include: a substance acting as an active ingredient for pharmaceutical products, veterinary pharmaceutical products, quasi-drugs, cosmetic products and agricultural chemicals; and a food additive. Synthetic or natural polymeric substances, which are generally referred to as resins or rubbers, are not included in the present poorly-soluble substance. The size of the poorly-soluble substance is not particularly limited. Its mean particle diameter is preferably 0.5 to 2000 µm, more preferably 1 to 200 µm, and further preferably 5 to 50 µm.

The poorly-soluble drug used in the present invention is a drug that is "sparingly soluble," "slightly soluble," "very slightly soluble," and "practically insoluble," which are defined in the Japanese Pharmacopoeia. The present poorly-soluble drug may have any dosage form of an oral preparation for internal application, an injection, a preparation for local administration, etc. Examples of such a poorly-soluble drug include an antitumor agent, an antibiotic, an antipyretic analgesic, an antihyperlipidemic agent, an antibacterial agent, a sedative hypnotic, a tranquilizer, an antiepileptic agent, an antidepressant, a gastrointestinal agent, an allergic disease therapeutic agent, an antihypertensive agent, a drug for arteriosclerosis, a blood circulation promoting agent, an antidiabetic agent, a hormonal agent, a fat-soluble vitamin, an anti-androgen agent, a cardiotonic drug, a drug for arrhythmia, a drug for diuresis, a local anesthetic, an anthelminthic, an antiarrhythmic agent, an anticoagulant, an antihistamic agent, an antimuscarinic agent, an antimycobacterial agent, an immunosuppressive agent, an antithyroid agent, an antiviral agent, an anxiolytic agent, an astringent, a β-adrenoreceptor blocker, an agent exerting inotropic action on cardiac muscle, a contrast medium, corticosteroid, a cough suppressing agent, a diagnostic agent, a diagnostic imaging agent, a diuretic, a dopamine agonist, a hemostatic agent, a lipid adjuster, a muscle relaxer, a parasympathetic drug, thyrocalcitonin and biphosphonate, prostaglandin, a radiopharmaceutical agent, sex hormone, a stimulant, an appetite suppressing agent, a sympathetic agent, a thyroid drug, a vasodilator, and xanthene.

Specific examples of the antitumor agent include HER2 inhibitors (heterocyclic compounds described in WO01/77107 and the like), melphalan, taxol, dacarbazine, doxorubicin hydrochloride, bleomycin hydrochloride, carmofur, methotrexate, enocitabine, etoposide, 5-fluorouracil, mitoxantrone, mesna, dimesna, aminoglutethimide, tamoxifen, acrolein, cisplatin, carboplatin, cyclophosphamide, lomustine, carmustine, cyclophosphamide, busulphan, para-aminosalicylic acid, mercaptopurine, tegafur, azathioprine, vinblastine sulfate, mitomycin C, ciclosporin, L-asparaginase, and ubenimex.

Examples of the antibiotic include amikacin, dibekacin, gentamycin, bacitracin, penicillin, cephalexin, tetracycline, streptomycin, nystatin, erythromycin, fradiomycin sulfate, chloramphenicol, cefmetazole, and tolnaftate.

Examples of the antipyretic analgesic include aspirin, aspirin aluminum, aminopyrine, phenacetin, mefenamic acid, flufenamic acid, flufenamic acid aluminum, tolfenamic acid, acemetacin, indomethacin, alclofenac, diclofenac, ibuprofen, ibuprofenpiconol, oxyphenbutazone, phenylbutazone, ketophenylbutazone, clofezone, tiaramide hydrochloride, ketoprofen, diclofenac sodium, sulindac, naproxen, fenbufen, flurbiprofen, fenprofen, bufexamac, mepirizole, perisoxal citrate, glafenine, bucolome, pentazocine, metiazinic acid, protizinic acid, pranoprofen, fenoprofen calcium, piroxicam, feprazone, fentiazac, bendazac, dimethylisopropylazulene, glycyrrhetic acid, bufexamac, salicylic acid, acetaminophen, methyl salicylate, glycol salicylate, bucolome, benzydamine, tialamide, tinoridine, ethenzamide, tenoxicam, chlortenoxicam, clidanac, naproxen, glycyrrhizin, glycyrrhetic acid, azulene, camphor, thymol, l-menthol, sasapyrine, alclofenac, diclofenac, suprofen, loxoprofen, diflunisal, tiaprofenic acid, oxaprozin, and felbinac.

Examples of the antihyperlipidemic agent include clinofibrate, clofibrate, fenofibrate, bezafibrate, cholestyramine, soysterol, tocopherol nicotinate, nicomol, niceritrol, probucol, simvastatin, colestimide, and elastase.

Examples of the antibacterial agent include ofloxacin, ciprofloxacin hydrochloride, tosufloxacin tosilate, norfloxacin, lomefloxacin hydrochloride, pazufloxacin, rokitamycin, cefpodoxime proxetil, roxithromycin, midecamycin acetate, cefatrizine, josamycin propionate, and fosfomycin or a salt thereof.

Examples of the sedative hypnotic include barbital, amobarbital, amobarbital sodium, phenobarbital, phenobarbital sodium, secobarbital sodium, pentobarbital calcium, hexobarbital, triclofos, bromovalerylurea, glutethimide, methaqualone, perlapine, nitrazepam, estazolam, flurazepam hydrochloride, flunitrazepam, and estazolam.

Examples of the tranquilizer include diazepam, lorazepam, and oxazolam.

Examples of the antiepileptic agent include phenyloin, phenobarbital, carbamazepine, primidone, phenacemide, ethylphenacemide, ethotoin, phensuximide, nitrazepam, and clonazepam.

Examples of the antidepressant include imipramine, noxiptiline, and phenelzine.

Examples of the gastrointestinal agent include aldioxa, irsogladine maleate, metoclopramide, cimetidine, famotidine, omeprazole, lansoprazole, enprostil, gefarnate, teprenone, sulpiride, trepibutone, oxethazain, and sucralfate.

Examples of the allergic disease therapeutic agent include clemastine fumarate, cyproheptadine hydrochloride, fexofenadine hydrochloride, ebastine, mequitazine, diphenhydramine, methdilazine, clemizole, and methoxyphenamine.

Examples of the antihypertensive agent include alacepril, nicardipine hydrochloride, delapril hydrochloride, captopril, cilnidipine, felodipine, barnidipine hydrochloride, efonidipine hydrochloride, amlodipine besylate, benidipine hydrochloride, nisoldipine, manidipine hydrochloride, nitrendipine, nilvadipine, trandolapril, valsartan, candesartan cilexetil, urapidil, carvedilol, prazosin hydrochloride, bunazosin hydrochloride, doxazosin mesilate, reserpine, methyldopa, guanabenz acetate, deserpidine, meptame, and meptamate.

Examples of the drug for arteriosclerosis include clofibrate, simfibrate, elastase, soysterol, and nicomol.

Examples of the blood circulation promoting agent include tocopherol acetate, benzyl nicotinate, tolazoline, verapamil, caffeine, cyclandelate, acetylcholine, and tocopherol nicotinate.

Examples of the antidiabetic agent include tolbutamide, glibenclamide, gliclazide, troglitazone, epalrestat, buformin, and metformin.

Examples of the hormonal agent include dexamethasone, dexamethasone acetate, betamethasone, betamethasone valerate, betamethasone dipropionate, beclometasone dipropionate, prednisolone, prednisolone valerate, prednisolone acetate, methylprednisolone, methylprednisolone acetate, hydrocortisone, hydrocortisone acetate, hydrocortisone acetate propionate, amcinonide, triamcinolone, triamcinolone acetonide, fluocinolone acetonide, hexestrol, methimazole, estriol, estriol tripropionate, clobetasone acetate, clobetasol propionate, fluocinonide, testosterone propionate, testosterone enanthate, fluoxymesterone, drostanolone propionate, estradiol benzoate, estradiol propionate, estradiol valerate, ethinylestradiol, mestranol, estriol benzoate diacetate, fluorometholone, fludroxycortide, diflucortolone valerate, halcinonide, progesterone, hydroxyprogesterone caproate, pregnanediol, medroxyprogesterone acetate, dimethisterone, norethisterone, allylestrenol, gestonorone caproate, and oxendolone.

Examples of the antiandrogen agent include oxendolone, allylestrenol, chlormadinone acetate, gestonorone caproate, osaterone acetate, flutamide, and bicalutamide.

Examples of the cardiotonic drug include digoxin, digotoxin, and ubidecarenone.

Examples of the drug for arrhythmia include pindolol, nadolol, bopindolol malonate, arotinolol hydrochloride, atenolol, lidocaine, propafenone hydrochloride, amiodarone hydrochloride, disopyramide, and carteolol hydrochloride.

Examples of the drug for diuresis include polythiazid, spironolactone, chlortalidone, triamteren, hydrochlorothiazide, and furosemide.

Examples of the local anesthetic include dibucaine hydrochloride, ethyl aminobenzoate, procaine hydrochloride, lidocaine, tetracaine hydrochloride, lidocaine hydrochloride, T-Cain, benzocaine, benzyl alcohol, pramoxine hydrochloride, quatacaine hydrochloride, butanicaine hydrochloride, piperocaine hydrochloride, and chlorobutanol.

Examples of the substance used in cosmetic products or quasi-drugs include methyl cinnamate, ethyl cinnamate, dl-α-tocopherol acetate, α-tocopherol (vitamin E), trichlorocarbanilide, eugenol, isoeugenol, ethyl methyl phenylglycidate, geranyl acetate, piperonal, hexyl laurate, ionone, cinnamyl acetate, decyl oleate, terpinyl acetate, triazine, anilide, benzophenone, triazole, cinnamide, sulfonated benzoimidazole, carotene, piroctone olamine, minoxidil, phytosteside, tocopherol nicotinate, ethinyl estradiol, polyporusterone, ecdysteroids, and various types of perfumes.

Examples of the substance used in food and drink products include L-ascorbyl stearate, benzoic acid, ionone, isoeugenol, ergocalciferol (vitamin $D_2$), eugenol, butyl parahydroxybenzoate, isopropyl parahydroxybenzoate, β-carotene, citronellyl formate, cholecalciferol (vitamin $D_3$), cinnamyl acetate, phenethyl acetate, ethyl cinnamate, dibutylhydroxytoluene, allyl hexanoate, propyl gallate, methyl β-methyl ketone, folic acid, riboflavine tetrabutyrate, lecithin, and dl-α-tocopherol.

Examples of the agricultural chemical include poorly-soluble agricultural chemical active ingredients having insecticidal action, germicidal action, herbicidal action, plant growth regulatory and other actions, such as a substance having a solubility in water (25° C.) of 1000 ppm or less.

Specifically, examples of the poorly-soluble insecticidal substance include abamectin, acrinathrin, amitraz, azadirachtin, azamethiphos, azinphos-methyl, azocyclotin, ethofenprox, ethylthiometon, chlorpyrifos methyl, bensultap, bifenthrin, bromopropylate, buprofezin, carbaryl, chlorfenapyr, chlorfenson, chlorfluazuron, clofentezine, coumaphos, diazinon, cycroprothrin, cyfluthrin, β-cyfluthrin, cypermethrin, α-cypermethrin, θ-cypermethrin, deltamethrin, diafehthiuron, dicofol, diflubenzuron, carbosulfan, endosulfan, esfenvalerate, etoxazole, fenazaquin, fenbutatin oxide, fenoxycarb, fenpyroximate, fipronil, fluazuron, flucycloxuron, flufenoxuron, flubendiamide, fenthion, halofenozide, hexaflumuron, hexythiazox, hydramethylnon, metaflumizone, lufenuron, methiocarb, methoxychlor, milbemycin, novaluron, pentachlorophenol, pyridaben, rotenone, sulfluramid, tebufenozide, tebufenpyrad, tebupirimfos, teflubenzuron, tetrachlorvinphos, tetradifon, thiodicarb, benfuracarb, tralomethrin, tolfenpyrad, triflumuron, trimethacarb, furathiocarb, and bendiocarb.

Examples of the poorly-soluble germicidal substance include azoxystrobin, isoprothiolane, benalaxyl, benomyl, bitertanol, bromuconazole, captafol, captan, carpropamide, carbendazim, chinomethionate, chlorothalonil, chlozolinate, cyprodinil, dichlofluanid, diclofen, diclomezine, dicloran, diclocymet, diethofencarb, dimethomorph, diniconazole, dithianon, tiadinil, epoxiconazole, famoxadone, fenarimol, fenbuconazole, fenfuram, fenpiclonil, fentin, fluazinam, fludioxonil, fluoroimide, fluquinconazole, flusulfamide, flutolanil, folpet, hexachlorobenzene, hexaconazole, imibenconazole, ipconazole, iprodione, kresoxim-methyl, manzeb, maneb, mepanipyrim, mepronil, metconazole, metiram, nickel bis(dimethyldithiocarbamate), nuarimol, oxine copper, oxolinic acid, pencycuron, phthalide, procymidone, propineb, quintozene, sulfur, tebuconazole, tecloftalam, tecnazene, thifluzamide, thiophanete-methyl, thiram, tolclofos-methyl, tolylfluanide, triadimefon, triadimenol, triazoxide, triforine, triticonazole, vinclozolin, zineb, and ziram.

Examples of the poorly-soluble herbicidal substance include azafenidin, thenylchlor, bifenox, sulfentrazone, pyraflufen-ethyl, flumiclorac-pentyl, flumioxazin, aclonifen, atrazine, indanofan, bensulfuron methyl, benzofenap, bromobutide, bromofenoxim, chlomethoxyfen, chlorbromuron, chlorimuron ethyl, chlornitrofen, chlortoluron, chlorthaldimethyl, clomeprop, dymron, desmedipham, dichlobenil, diflufenican, dimefuron, dinitramine, diuron, ethametsulfuron methyl, traiziflam, fenoxaprop-ethyl, flamprop-methyl, flazasulfuron, flumetsulam, fluthiacet-methyl, flupoxam, fluridone, flurtamone, oxaziclomefone, isoproturon, isoxaben, isoxapyrifop, lactofen, lenacil, linuron, mefenacet, methabenzthiazuron, metobenzuron, naproanilide, neburon, norflurazon, oryzalin, oxadiazon, oxyfluorfen, phenmedipham, prodiamine, prometryn, propazine, propyzamide, pyrazolynate, pyrazosulfuron-ethyl, pyributicarb, quinclorac, quizalofop ethyl, rimsulfuron, siduron, simazine, terbuthylazine, terbutryn, thiazopyr, tralkoxydim, and trietazine.

Examples of the poorly-soluble plant growth regulatory substance include 6-benzylaminopurine, cyclanilide, flumetralin, forchlorfenuron, inabenfide, 2-(1-naphtyl)acetamide, paclobutrazol, n-phenylphthalamidic acid, thidiazuron, and uniconazole.

The substance with improved aqueous solubility obtained by the production method of the present invention can be used by mixing it into pharmaceutical products, veterinary pharmaceutical products, quasi-drugs, cosmetic products, agricultural chemicals, food products, and the like. The forms of the pharmaceutical products, veterinary pharmaceutical products, quasi-drugs, cosmetic products, agricultural chemicals, and food products are not particularly limited. The forms may be either solid compositions such as a tablet, granule or powder, or aqueous liquid compositions containing water. As a result of the improvement of solubility according to the present invention, a substance, which has not sufficiently exhibited effects due to its poor solubility, can exhibit the effects.

EXAMPLES

1. [Preparation of Coating Agent]
A. [Preparation of Hydroxyapatite Microparticles]

A phosphoric acid aqueous solution in a 30 wt % concentration was added dropwise to a calcium hydroxide suspension under stirring, until the Ca/P ratio became 1.67. The thus generated gelatinous substance was left at a room temperature for 1 day, so as to age it. Thereafter, this gelatinous substance was filtrated with a glass filter, and the remaining substance was then dried in the air at 100° C. The resultant was ground with a mixer, so as to obtain hydroxyapatite.

Such hydroxyapatite was suspended in water to prepare a 20% suspension. This suspension was then ground employing Dino Mill (ECM-PILOT, manufactured by Willy A. Baechofen AG Machinenfabrik Basel) using 0.3-mm zirconia beads. Particle size distribution was measured every 30 minutes, and the grinding was terminated at the time point in which almost no change was observed in terms of particle size, thereby obtaining hydroxyapatite microparticles.

B. [Preparation of pH Adjuster and Surfactant]

A pH adjuster and a surfactant were each crushed in a mortar, and they were then passed through a 150-μm mesh sieve. The resultants were used in experiments.

2. [Preparation of Substance with Improved Aqueous Solubility]

A. [Coating of Poorly-Soluble Substance with Hydroxyapatite Microparticles Using Mechanofusion System]

Using Mechanofusion System AMS-MINI-GMP (manufactured by Hosokawa Micron Group), a poorly-soluble substance was coated with hydroxyapatite microparticles.

A poorly-soluble substance and hydroxyapatite microparticles were placed into a Mechanofusion System Device while changing the ratio between the poorly-soluble substance and the hydroxyapatite microparticles. They were placed in the device to a total amount of 90 g/once, and thereafter, a coating treatment was carried out. During the coating treatment, the jacket portion of the device was cooled with alcohol, so that the temperature of the portion became 20° C. or lower. Moreover, in order to prevent the rotation load from exceeding 2.0 A, the coating treatment was carried out at a rotation number of 1,250 to 4,000 rpm for 15 to 60 minutes. In the case of products, which could be subjected to a coating treatment at a rotation number of 4,000 rpm, the coating treatment was carried out for 15 minutes. On the other hand, in the case of products whose rotation load exceeded 2.0 A, and consequently, the rotation number became 4,000 rpm or less, a coating treatment time was increased due to the rotation number. Thus, a coating treatment was carried out at the fewest rotation number (1,250 rpm) for 60 minutes as the longest coating treatment time.

The coated substance was recovered, and thereafter, ground pH adjuster and/or surfactant were added to the recovered substance in an amount of 1/100 to 3 times the amount of the poorly-soluble substance. The obtained mixture was subjected to Mechanofusion Device again, so as to produce a final pharmaceutical preparation. Thereby, there was obtained a pharmaceutical preparation, in which the outermost layer of a pharmaceutical preparation formed by coating a poorly-soluble substance with hydroxyapatite microparticles was coated with a pH adjuster and/or a surfactant.

B. [Coating of Poorly-Soluble Substance with Hydroxyapatite Microparticles According to Hybridization System]

Using Hybridization System NHS-1 (manufactured by Nara Machinery Co., Ltd.), a poorly-soluble substance was coated with calcium compound microparticles.

A mixture that had previously been prepared by mixing a poorly-soluble substance with hydroxyapatite microparticles was placed in the Hybridization System, while changing the ratio between the poorly-soluble substance and the hydroxyapatite microparticles. They were placed in the system to a total amount of 100 g/once, and thereafter, a coating treatment was carried out at 3,000 rpm for 5 minutes.

The resultant was recovered, and thereafter, ground pH adjuster and/or surfactant were added thereto in an amount of 1/100 to 3 times the amount of the poorly-soluble substance. The obtained mixture was again subjected to Hybridization System, so as to produce a final pharmaceutical preparation. Thereby, there was obtained a pharmaceutical preparation, in which the outermost layer of a pharmaceutical preparation formed by coating a poorly-soluble substance with hydroxyapatite microparticles was coated with a pH adjuster and/or a surfactant.

3. [Dissolution Test of Poorly-soluble Substances]

A poorly-soluble substance coated with calcium compound microparticles (a substance with improved aqueous solubility) and a test solution (50 mL) were placed in a 50-mL screw cap centrifuge tube made of glass. From initiation of the test, the mixed solution was stirred with a stirrer having a length of 15 mm. The rotation number of the stirrer was 120 rpm, and all of the tests were conducted in a thermostat at 37±0.5° C. Two types of test solutions, namely, distilled water and 2nd fluid for disintegration test (pH 6.8) of the Japanese Pharmacopoeia were used. As such 2nd fluid for disintegration test of the Japanese Pharmacopoeia, a solution prepared by diluting the 10-fold concentration solution of Kanto Kagaku Co., Ltd. with distilled water was used. With regard to the amount of a substance with improved aqueous solubility used in the dissolution test, a preliminary test was carried out on each substance with improved aqueous solubility several times according to the above described method, and the amount of the substance with improved aqueous solubility used in the dissolution test was defined as an amount approximately two times the amount of the substance with improved aqueous solubility dissolved for 360 minutes.

A comparative test was carried out in the same manner as that described above, with the exception that, instead of a substance with improved aqueous solubility coated with hydroxyapatite microparticles and with a pH adjuster and/or a surfactant, a poorly-soluble substance or the like was used in the same amount as the substance with improved aqueous solubility.

1 mL of the solution was sampled in an Eppendorf centrifuge tube, 1, 3, 10, 30, 60, 180 and 360 minutes after initiation of the test. The thus sampled solution was centrifuged at 12,000 rpm for 5 minutes. Thereafter, the substance with improved aqueous solubility and hydroxyapatite microparticles, which had not been dissolved in the solution, were removed. In the case of the comparative test, the poorly-soluble substance or the like, which had not been dissolved in the solution, was removed. An aliquot of this supernatant was immediately frozen. The frozen sample was freeze-dried, and it was then used as a sample in the measurement of the amount of the substance with improved aqueous solubility, which had been dissolved in the test solution. The dissolved poorly-soluble substance was measured mainly using a dual wavelength absorption photometer.

3-1. [Dissolved Amounts of Poorly-soluble Substances after Dissolution Test for 360 Minutes]

1. Tolbutamide

TABLE 1

| | | Coating agent | | | | | Dissolved |
|---|---|---|---|---|---|---|---|
| | Coating method | Ingredient | Particle diameter | Additive | Coating rate | Dissolution test medium | amount (μg/ml) |
| Example 1-1 | Mechanofusion System | Hydroxyapatite | 100 nm | Disodium hydrogenphosphate 1/10 | 100% | Distilled water | 7101.4 |
| | | | | | | Second disintegration test medium | 5250.4 |
| Example 1-2 | Mechanofusion System | Hydroxyapatite | 100 nm | Disodium hydrogenphosphate 1/5 | 100% | Distilled water | 8502.0 |
| | | | | | | Second disintegration test medium | 6098.6 |
| Example 1-3 | Mechanofusion System | Hydroxyapatite | 50 nm | Disodium hydrogenphosphate 1/5 | 100% | Distilled water | 8792.7 |
| | | | | | | Second disintegration test medium | 7883.4 |
| Example 1-4 | Mechanofusion System | Hydroxyapatite | 100 nm | L-Arginine 1/5 | 100% | Distilled water | 8391.2 |
| | | | | | | Second disintegration test medium | 5766.8 |
| Example 1-5 | Mechanofusion System | Hydroxyapatite | 100 nm | SDS1/5 | 100% | Distilled water | 8678.0 |
| | | | | | | Second disintegration test medium | 6319.3 |
| Example 1-6 | Mechanofusion System | Hydroxyapatite | 100 nm | Disodium hydrogenphosphate 1/10 SDS1/10 | 100% | Distilled water | 7498.7 |
| | | | | | | Second disintegration test medium | 5685.3 |
| Comparative Example 1-1 | Mechanofusion System | Hydroxyapatite | 100 nm | Not used | 100% | Distilled water | 2584.0 |
| | | | | | | Second disintegration test medium | 4913.4 |
| Comparative Example 1-2 | Mechanofusion System | Not used | | Disodium hydrogenphosphate 1/5 | 100% | Distilled water | 133.3 |
| | | | | | | Second disintegration test medium | 532.1 |
| Comparative Example 1-3 | Mechanofusion System | Not used | | L-Arginine 1/5 | 100% | Distilled water | 768.4 |
| | | | | | | Second disintegration test medium | 1792.4 |
| Comparative Example 1-4 | Mechanofusion System | Not used | | SDS1/5 | 100% | Distilled water | 302.5 |
| | | | | | | Second disintegration test medium | 1862.3 |
| Comparative Example 1-5 | | Tolbutamide | | | | Distilled water | 68.6 |
| | | | | | | Second disintegration test medium | 2429.1 |

2. Bezafibrate

TABLE 2

| | Coating method | Coating agent | | | Coating rate | Dissolution test medium | Dissolved amount (μg/ml) |
|---|---|---|---|---|---|---|---|
| | | Ingredient | Grinding | Additive | | | |
| Example 2-1 | Hybridization System | Hydroxyapatite | 100 nm | Disodium hydrogenphosphate 1/100 | 100% | Distilled water<br>Second disintegration test medium | 7426.9<br>7012.8 |
| Example 2-2 | Hybridization System | Hydroxyapatite | 100 nm | Disodium hydrogenphosphate 1/10 | 100% | Distilled water<br>Second disintegration test medium | 13498.4<br>11743.6 |
| Example 2-3 | Hybridization System | Hydroxyapatite | 10 μm | Disodium hydrogenphosphate 1/5 | 100% | Distilled water<br>Second disintegration test medium | 9193.2<br>9046.5 |
| Example 2-4 | Hybridization System | Hydroxyapatite | 100 nm | Disodium hydrogenphosphate 1/5 | 100% | Distilled water<br>Second disintegration test medium | 14741.2<br>12127.5 |
| Example 2-5 | Hybridization System | Hydroxyapatite | 100 nm | Disodium hydrogenphosphate 1/5 | 50% | Distilled water<br>Second disintegration test medium | 13702.5<br>11171.8 |
| Example 2-6 | Hybridization System | Hydroxyapatite | 100 nm | Disodium hydrogenphosphate 1/5 | 10% | Distilled water<br>Second disintegration test medium | 11856.2<br>10572.2 |
| Example 2-7 | Hybridization System | Hydroxyapatite | 50 nm | Disodium hydrogenphosphate 1/5 | 100% | Distilled water<br>Second disintegration test medium | 12101.2<br>11116.2 |
| Example 2-8 | Hybridization System | Hydroxyapatite | 100 nm | Disodium hydrogenphosphate 3/1 | 100% | Distilled water<br>Second disintegration test medium | 8363.0<br>3876.7 |
| Example 2-9 | Hybridization System | Hydroxyapatite | 100 nm | L-Arginine 1/5 | 10% | Distilled water<br>Second disintegration test medium | 16703.3<br>12298.4 |
| Example 2-10 | Hybridization System | Hydroxyapatite | 100 nm | Sodium hydrogencarbonate 1/5 | 100% | Distilled water<br>Second disintegration test medium | 19659.9<br>15898.4 |
| Example 2-11 | Hybridization System | Hydroxyapatite | 100 nm | SDS 1/5 | 100% | Distilled water<br>Second disintegration test medium | 18239.1<br>15137.5 |
| Comparative Example 2-1 | Hybridization System | Hydroxyapatite | 100 nm | Not used | 100% | Distilled water<br>Second disintegration test medium | 3440.3<br>6538.0 |
| Comparative Example 2-2 | Mixing | Hydroxyapatite | 100 nm | Not used | 100% | Distilled water<br>Second disintegration test medium | 101.2<br>2254.3 |
| Comparative Example 2-3 | Hybridization System | Not used | | Disodium hydrogenphosphate 1/5 | 100% | Distilled water<br>Second disintegration test medium | 181.3<br>1180.0 |
| Comparative Example 2-4 | Hybridization System | Not used | | Sodium hydrogencarbonate 1/5 | 100% | Distilled water<br>Second disintegration test medium | 944.1<br>4154.3 |
| Comparative Example 2-5 | Hybridization System | Not used | | SDS 1/5 | 100% | Distilled water<br>Second disintegration test medium | 1012.0<br>9984.8 |
| Comparative Example 2-6 | | Bezafibrate | | | | Distilled water<br>Second disintegration test medium | 13.2<br>3096.6 |

3. Famotidine

TABLE 3

| | Coating method | Coating agent | | | Coating rate | Dissolution test medium | Dissolved amount (μg/ml) |
|---|---|---|---|---|---|---|---|
| | | Ingredient | Grinding | Additive | | | |
| Example 3-1 | Mechanofusion System | Hydroxyapatite | 100 nm | Citric acid 1/5 | 100% | Distilled water<br>Second disintegration test medium | 11365.1<br>10710.8 |
| Example 3-2 | Mechanofusion System | Hydroxyapatite | 100 nm | SDS 1/5 | 100% | Distilled water<br>Second disintegration test medium | 2380.6<br>4929.7 |
| Comparative Example 3-1 | Mechanofusion System | Hydroxyapatite | 100 nm | Not used | 100% | Distilled water<br>Second disintegration test medium | 1671.5<br>2698.4 |

TABLE 3-continued

|  | Coating method | Coating agent | | Coating rate | Dissolution test medium | Dissolved amount (μg/ml) |
|---|---|---|---|---|---|---|
|  |  | Ingredient | Grinding | Additive |  |  |
| Comparative Example 3-2 | Mechanofusion System | Not used |  | Citric acid 1/5 | 100% | Distilled water<br>Second disintegration test medium | 956.5<br>1468.1 |
| Comparative Example 3-3 | Mechanofusion System | Not used |  | SDS 1/5 | 100% | Distilled water<br>Second disintegration test medium | 1580.0<br>1809.2 |
| Comparative Example 3-4 |  | Famotidine |  |  |  | Distilled water<br>Second disintegration test medium | 1497.4<br>2410.4 |

4. Trimethoprim

TABLE 4

|  | Coating method | Coating agent | | | Coating rate | Dissolution test medium | Dissolved amount (μg/ml) |
|---|---|---|---|---|---|---|---|
|  |  | Ingredient | Grinding | Additive |  |  |  |
| Example 4-1 | Hybridization System | Hydroxyapatite | 100 nm | Citric acid 1/5 | 100% | Distilled water<br>Second disintegration test medium | 10144.4<br>13265.3 |
| Comparative Example 4-1 | Hybridization System | Hydroxyapatite | 100 nm | Not used | 100% | Distilled water<br>Second disintegration test medium | 1212.6<br>2532.6 |
| Comparative Example 4-2 | Hybridization System | Not used |  | Citric acid 1/5 | 100% | Distilled water<br>Second disintegration test medium | 806.9<br>1985.0 |
| Comparative Example 4-3 |  | Trimethoprim |  |  |  | Distilled water<br>Second disintegration test medium | 656.3<br>1321.9 |

5. Probucol

TABLE 5

|  | Coating method | Coating agent | | | Coating rate | Dissolution test medium | Dissolved amount (μg/ml) |
|---|---|---|---|---|---|---|---|
|  |  | Ingredient | Grinding | Additive |  |  |  |
| Example 5-1 | Mechanofusion System | Hydroxyapatite | 100 nm | Disodium hydrogenphosphate 1/5 | 100% | Distilled water<br>Second disintegration test medium | 561.5<br>332.4 |
| Comparative Example 5-1 | Mechanofusion System and Mixing(* | Hydroxyapatite | 100 nm | Disodium hydrogenphosphate 1/5 | 100% | Distilled water<br>Second disintegration test medium | 289.1<br>180.6 |
| Comparative Example 5-2 |  | Probucol |  |  |  | Distilled water<br>Second disintegration test medium | 9.7<br>28.0 |

*Probucol was coated with hydroxyapatite using Mechanofusion System, and disodium hydrogen phosphate was then mixed therein.

6. Sulpiride

TABLE 6

|  | Coating method | Coating agent | | | Coating rate | Dissolution test medium | Dissolved amount (μg/ml) |
|---|---|---|---|---|---|---|---|
|  |  | Ingredient | Grinding | Additive |  |  |  |
| Example 6-1 | Mechanofusion System | Hydroxyapatite | 100 nm | Citric acid 1/100 | 100% | Distilled water<br>Second disintegration test medium | 12814.7<br>18099.7 |
| Example 6-2 | Mechanofusion System | Hydroxyapatite | 100 nm | Citric acid 1/5 | 100% | Distilled water<br>Second disintegration test medium | 35293.4<br>38081.1 |

TABLE 6-continued

|  | Coating method | Coating agent | | | Coating rate | Dissolution test medium | Dissolved amount (μg/ml) |
|---|---|---|---|---|---|---|---|
|  |  | Ingredient | Grinding | Additive |  |  |  |
| Example 6-3 | Mechanofusion System | Hydroxyapatite | 100 nm | Citric acid 3/1 | 100% | Distilled water<br>Second disintegration test medium | 18186.7<br>23748.5 |
| Example 6-4 | Mechanofusion System | Hydroxyapatite | 100 nm | SDS1/100 | 100% | Distilled water<br>Second disintegration test medium | 6695.6<br>9735.7 |
| Example 6-5 | Mechanofusion System | Hydroxyapatite | 100 nm | SDS1/5 | 100% | Distilled water<br>Second disintegration test medium | 6923.0<br>13619.7 |
| Example 6-6 | Mechanofusion System | Hydroxyapatite | 100 nm | SDS3/1 | 100% | Distilled water<br>Second disintegration test medium | 22631.4<br>27321.3 |
| Comparative Example 6-1 | Mechanofusion System | Hydroxyapatite | 100 nm | Not used | 100% | Distilled water<br>Second disintegration test medium | 1144.8<br>6459.8 |
| Comparative Example 6-2 | Mechanofusion System | Not used | | Citric acid 1/5 | 100% | Distilled water<br>Second disintegration test medium | 1733.0<br>5700.0 |
| Comparative Example 6-3 | Mechanofusion System | Not used | | SDS1/5 | 100% | Distilled water<br>Second disintegration test medium | 2425.0<br>3746.2 |
| Comparative Example 6-4 | | Sulpiride | | | | Distilled water<br>Second disintegration test medium | 715.8<br>6866.1 |

7. Lidocaine

TABLE 7

|  | Coating method | Coating agent | | | Coating rate | Dissolution test medium | Dissolved amount (μg/ml) |
|---|---|---|---|---|---|---|---|
|  |  | Ingredient | Grinding | Additive |  |  |  |
| Example 7-1 | Mechanofusion System | Hydroxyapatite | 100 nm | Citric acid 1/5 | 100% | Distilled water<br>Second disintegration test medium | 29934.4<br>35102.5 |
| Comparative Example 7-1 | Mechanofusion System | Hydroxyapatite | 100 nm | Not used | 100% | Distilled water<br>Second disintegration test medium | 4528.8<br>8760.0 |
| Comparative Example 7-2 | Mechanofusion System | Not used | | Citric acid 1/5 | 100% | Distilled water<br>Second disintegration test medium | 3582.6<br>6360.1 |
| Comparative Example 7-3 | | Lidocaine | | | | Distilled water<br>Second disintegration test medium | 3248.6<br>5469.0 |

8. Alacepril

TABLE 8

|  | Coating method | Coating agent | | | Coating rate | Dissolution test medium | Dissolved amount (μg/ml) |
|---|---|---|---|---|---|---|---|
|  |  | Ingredient | Grinding | Additive |  |  |  |
| Example 8-1 | Mechanofusion System | Hydroxyapatite | 100 nm | Disodium hydrogenphosphate 1/5 | 100% | Distilled water<br>Second disintegration test medium | 26119.0<br>27527.2 |
| Example 8-2 | Mechanofusion System | Hydroxyapatite | 100 nm | Disodium hydrogenphosphate 1/4 | 100% | Distilled water<br>Second disintegration test medium | 31636.7<br>32384.9 |
| Comparative Example 8-1 | | Alacepril | | | | Distilled water<br>Second disintegration test medium | 996.5<br>2548.2 |

9. Erythromycin

TABLE 9

| | Coating method | Coating agent | | | Coating rate | Dissolution test medium | Dissolved amount (µg/ml) |
|---|---|---|---|---|---|---|---|
| | | Ingredient | Grinding | Additive | | | |
| Example 9-1 | Mechanofusion System | Hydroxyapatite | 100 nm | Citric acid 1/5 | 100% | Distilled water<br>Second disintegration test medium | 25648.9<br>21844.7 |
| Comparative Example 9-1 | | Erythromycin | | | | Distilled water<br>Second disintegration test medium | 846.1<br>6044.7 |

10. Haloperidol

TABLE 10

| | Coating method | Coating agent | | | Coating rate | Dissolution test medium | Dissolved amount (µg/ml) |
|---|---|---|---|---|---|---|---|
| | | Ingredient | Grinding | Additive | | | |
| Example 10-1 | Hybridization System | Hydroxyapatite | 100 nm | Citric acid 1/5 | 100% | Distilled water<br>Second disintegration test medium | 562.7<br>148.6 |
| Comparative Example 10-1 | | Haloperidol | | | | Distilled water<br>Second disintegration test medium | 13.1<br>48.9 |

3-2. [Dissolution Time and Dissolved Amount]
1. Tolbutamide
Dissolution Test Using Water Dissolved Amount (µg/ml)

TABLE 11

| Example No. | Coating ingredient | Elution time (min) | | | | | | |
|---|---|---|---|---|---|---|---|---|
| | | 1 | 3 | 10 | 30 | 60 | 180 | 360 |
| Example 1-1 | Disodium hydrogenphosphate 1/10 + 100 nm HAP | 6704.6 | 6852.3 | 6925.9 | 7441.6 | 7339.2 | 6735.4 | 7101.4 |
| Example 1-2 | Disodium hydrogenphosphate 1/5 + 100 nm HAP | 7087.3 | 7936.0 | 8375.1 | 8201.9 | 8391.2 | 8344.4 | 8502.0 |
| Example 1-3 | Disodium hydrogenphosphate 1/5 + 50 nm HAP | 7057.9 | 7507.7 | 8036.5 | 8160.2 | 8320.0 | 8514.3 | 8792.7 |
| Example 1-4 | L-Arginine 1/5 + 100 nm HAP | 8646.2 | 8646.7 | 7654.3 | 8085.7 | 8281.3 | 8206.4 | 8391.2 |
| Example 1-5 | SDS1/5 + 100 nm HAP | 4349.4 | 6817.6 | 7650.9 | 7769.1 | 8061.2 | 8096.9 | 8678.0 |
| Example 1-6 | Disodium hydrogenphosphate 1/10 + SDS1/10 + 100 nm HAP | 5711.7 | 7004.1 | 7327.2 | 7795.4 | 7188.8 | 7314.1 | 7498.7 |
| Comparative Example 1-1 | 100 nm HAP | 2114.6 | 2421.2 | 2592.4 | 2591.9 | 2559.5 | 2574.2 | 2584.0 |
| Comparative Example 1-2 | Disodium hydrogenphosphate 1/5 | 105.7 | 122.1 | 120.6 | 131.8 | 135.8 | 131.9 | 133.3 |
| Comparative Example 1-3 | L-Arginine 1/5 | 27.47 | 139.6 | 1352.9 | 1451.8 | 963.8 | 838.6 | 768.4 |
| Comparative Example 1-4 | SDS1/5 | 591.6 | 265.6 | 384.1 | 248.7 | 402.5 | 271.1 | 302.5 |
| Comparative Example 1-5 | — | 48.8 | 49.3 | 51.3 | 56.6 | 50.5 | 52.9 | 68.6 |

Dissolution Test Using 2nd Fluid for Disintegration Test Dissolved Amount (µg/ml)

TABLE 12

| Example No. | Coating ingredient | Elution time (min) | | | | | | |
|---|---|---|---|---|---|---|---|---|
| | | 1 | 3 | 10 | 30 | 60 | 180 | 360 |
| Example 1-1 | Disodium hydrogenphosphate 1/10 + 100 nm HAP | 3565.5 | 4545.7 | 5122.9 | 5020.9 | 5111.2 | 5291.2 | 5250.4 |

TABLE 12-continued

| Example No. | Coating ingredient | Elution time (min) | | | | | | |
|---|---|---|---|---|---|---|---|---|
| | | 1 | 3 | 10 | 30 | 60 | 180 | 360 |
| Example 1-2 | Disodium hydrogenphosphate 1/5 + 100 nm HAP | 4286.1 | 5122.4 | 6100.4 | 6192.9 | 6005.6 | 6125.2 | 6098.6 |
| Example 1-3 | Disodium hydrogenphosphate 1/5 + 50 nm HAP | 7990.5 | 6127.2 | 7111.8 | 7786.1 | 8171.6 | 7721.9 | 7883.4 |
| Example 1-4 | L-Arginine 1/5+100 nm HAP | 3475.7 | 5015.5 | 6141.8 | 6110.3 | 5602.3 | 5749.3 | 5766.8 |
| Example 1-5 | SDS1/5 + 100 nm HAP | 2530.3 | 4384.8 | 5171.2 | 5493.5 | 5496.8 | 5563.4 | 6319.3 |
| Example 1-6 | Disodium hydrogenphosphate 1/5 + SDS1/5 + 100 nm HAP | 2975.1 | 4814.9 | 5513.8 | 5579.8 | 5461.1 | 5639.1 | 5685.3 |
| Comparative Example 1-1 | 100 nm HAP | 3603.0 | 3915.4 | 4265.2 | 4428.8 | 4554.5 | 4907.2 | 4913.4 |
| Comparative Example 1-2 | Disodium hydrogenphosphate 1/5 | 525.4 | 475.1 | 495.7 | 522.9 | 447.3 | 480.8 | 532.1 |
| Comparative Example 1-3 | L-Arginine 1/5 | 4.1 | 53.7 | 960.2 | 1084.2 | 1289.6 | 2249.2 | 1792.4 |
| Comparative Example 1-4 | SDS1/5 | 1426.8 | 1493.2 | 1584.9 | 2048.7 | 1803.4 | 1732.1 | 1862.3 1000.1 |
| Comparative Example 1-5 | — | 637.3 | 1597.2 | 2041.9 | 2141.1 | 2449.4 | 2432.9 | 2429.1 |

2. Bezafibrate
Dissolution Test Using Water Dissolved Amount (μg/ml)

TABLE 13

| Example No. | Coating ingredient | Elution time (min) | | | | | | |
|---|---|---|---|---|---|---|---|---|
| | | 1 | 3 | 10 | 30 | 60 | 180 | 360 |
| Example 2-1 | Disodium hydrogenphosphate 1/100 +100 nm HAP | 4737.3 | 5876.1 | 6713.0 | 7541.3 | 7586.6 | 7418.3 | 7426.9 |
| Example 2-2 | Disodium hydrogenphosphate 1/10+100 nm HAP | 13217.0 | 15062.8 | 15145.3 | 15844.6 | 15564.2 | 15120.3 | 13498.4 |
| Example 2-3 | Disodium hydrogenphosphate 1/5 + 10 μm HAP | 4636.4 | 8858.2 | 9102.6 | 9060.9 | 8963.1 | 9137.1 | 9193.2 |
| Example 2-4 | Disodium hydrogenphosphate 1/5 + 100 nm HAP | 17967.4 | 15876.7 | 16846.8 | 16067.0 | 16028.1 | 15617.9 | 14741.2 |
| Example 2-5 | Disodium hydrogenphosphate 1/5 + 100 nm HAP 50% | 6256.9 | 10918.7 | 13350.3 | 13610.5 | 13443.7 | 12776.5 | 13702.5 |
| Example 2-6 | Disodium hydrogenphosphate 1/5 + 100 nm HAP 10% | 8323.2 | 10646.9 | 13714.0 | 12353.8 | 12176.9 | 12438.6 | 11856.2 |
| Example 2-7 | Disodium hydrogenphosphate 1/5 + 50 nm HAP | 11379.8 | 12048.4 | 12414.6 | 12314.5 | 12269.4 | 12228.2 | 12101.2 |
| Example 2-8 | Disodium hydrogenphosphate 3/1 + 100 nm HAP | 12228.2 | 6070.3 | 6648.1 | 6950.0 | 7682.6 | 7745.1 | 8363.0 |
| Example 2-9 | L-Arginine 1/5 + 100 nm HAP | 10840.7 | 14993.9 | 18099.3 | 18051.1 | 18020.0 | 17792.8 | 16703.3 |
| Example 2-10 | Sodium hydrogencarbonate 1/5 + 100 nm HAP | 9297.8 | 10413.7 | 12546.4 | 14638.3 | 18502.6 | 19699.7 | 19659.9 |
| Example 2-11 | SDS1/5 + 100 nm HAP | 9504.9 | 13499.3 | 17515.4 | 16393.7 | 16303.5 | 18451.5 | 18239.1 |
| Comparative Example 2-1 | 100 nm HAP | 2758.5 | 2941.9 | 3161.9 | 3336.4 | 3289.5 | 3392.2 | 3440.3 |
| Comparative Example 2-2 | 100 nm HAP(Mixing) | 55.5 | 78.0 | 81.3 | 86.0 | 86.1 | 97.1 | 101.2 |
| Comparative Example 2-3 | Disodium hydrogenphosphate 1/5 | 137.9 | 146.5 | 166.3 | 169.4 | 171.9 | 178.7 | 181.3 |
| Comparative Example 2-4 | Sodium hydrogencarbonate 1/5 | 53.0 | 119.7 | 491.6 | 587.0 | 734.1 | 868.4 | 944.1 |
| Comparative Example 2-5 | SDS1/5 | 975.4 | 993.9 | 1027.4 | 900.6 | 957.8 | 1096.5 | 1012.0 |
| Comparative Example 2-6 | — | 10.4 | 11.6 | 10.9 | 11.9 | 12.3 | 12.9 | 13.2 |

Dissolution Test Using 2nd Fluid for Disintegration Test Dissolved Amount (μg/ml)

TABLE 14

| Example No. | Coating ingredient | Elution time (min) | | | | | | |
|---|---|---|---|---|---|---|---|---|
| | | 1 | 3 | 10 | 30 | 60 | 180 | 360 |
| Example 2-1 | Disodium hydrogenphosphate 1/100 + 100 nm HAP | 4211.0 | 5587.1 | 7230.7 | 6592.2 | 7278.1 | 6956.5 | 7012.8 |
| Example 2-2 | Disodium hydrogenphosphate 1/10 + 100 nm HAP | 12093.5 | 13293.2 | 13272.6 | 13367.0 | 13197.8 | 12777.9 | 11743.6 |
| Example 2-3 | Disodium hydrogenphosphate 1/5 + 10 μm HAP | 6016.8 | 8271.5 | 8833.7 | 8695.7 | 8957.4 | 8830.8 | 9046.5 |
| Example 2-4 | Disodium hydrogenphosphate 1/5 + 100 nm HAP | 13713.6 | 14009.3 | 14225.5 | 14026.1 | 13727.0 | 12809.1 | 12127.5 |
| Example 2-5 | Disodium hydrogenphosphate 1/5 + 100 nm HAP 50% | 6606.4 | 9820.1 | 10783.5 | 10760.5 | 11134.4 | 11360.2 | 11171.8 |
| Example 2-6 | Disodium hydrogenphosphate 1/5 + 100 nm HAP 10% | 8198.1 | 10217.0 | 11683.7 | 10868.4 | 10727.5 | 10904.3 | 10572.2 |
| Example 2-7 | Disodium hydrogenphosphate 1/5 + 50 nm HAP | 10298.0 | 10901.0 | 11256.1 | 11263.8 | 10808.5 | 11082.6 | 11116.2 |
| Example 2-8 | Disodium hydrogenphosphate 3/1 + 100 nm HAP | 8708.1 | 5416.7 | 4150.6 | 3734.3 | 3510.0 | 3328.8 | 3876.7 |
| Example 2-9 | L-Arginine 1/5 + 100 nm HAP | 9550.0 | 11264.5 | 13296.1 | 12841.7 | 13123.6 | 12817.2 | 12298.4 |
| Example 2-10 | Sodium hydrogencarbonate 1/5 + 100 nm HAP | 8616.7 | 10460.1 | 12709.6 | 12239.0 | 12363.7 | 15308.2 | 15898.4 |
| Example 2-11 | SDS1/5 + 100 nm HAP | 9409.0 | 11134.8 | 14379.2 | 15139.0 | 14282.8 | 15520.0 | 15137.5 |
| Comparative Example 2-1 | 100 nm HAP | 4840.4 | 5420.0 | 5773.4 | 5840.2 | 5976.7 | 6107.3 | 6538.0 |
| Comparative Example 2-2 | 100 nm HAP (Mixing) | 1754.3 | 1864.8 | 2229.6 | 2267.6 | 2224.5 | 2282.7 | 2254.3 |
| Comparative Example 2-3 | Disodium hydrogenphosphate 1/5 | 850.7 | 920.8 | 1108.1 | 1152.0 | 1174.0 | 1170.1 | 1180.0 |
| Comparative Example 2-4 | Sodium hydrogencarbonate 1/5 | 706.8 | 1036.8 | 2704.9 | 3285.6 | 3458.7 | 3753.2 | 4154.3 |
| Comparative Example 2-5 | SDS1/5 | 5724.4 | 8390.5 | 8781.9 | 9118.3 | 9124.5 | 8958.0 | 9984.8 |
| Comparative Example 2-6 | — | 805.1 | 2552.5 | 2866.5 | 2942.6 | 2965.5 | 3031.4 | 3096.6 |

3. Famotidine

Dissolution Test Using Water Dissolved Amount (μg/ml)

TABLE 15

| Example No. | Coating ingredient | Elution time (min) | | | | | | |
|---|---|---|---|---|---|---|---|---|
| | | 1 | 3 | 10 | 30 | 60 | 180 | 360 |
| Example 3-1 | Citric acid 1/5 100 nm HAP | 7688.1 | 10183.6 | 11246.5 | 11673.1 | 11584.5 | 11519.7 | 11365.1 |
| Example 3-2 | SDS1/5 100 nm HAP | 905.7 | 1412.1 | 2018.2 | 2294.1 | 2470.4 | 2555.6 | 2380.6 |
| Comparative Example 3-1 | 100 nm HAP | 1080.2 | 1269.9 | 1616.6 | 1834.6 | 1819.8 | 1778.1 | 1671.5 |
| Comparative Example 3-2 | Citric acid 1/5 | 402.2 | 363.0 | 415.4 | 915.3 | 850.3 | 983.5 | 956.5 |
| Comparative Example 3-3 | SDS1/5 | 777.7 | 1011.1 | 1646.6 | 1606.8 | 1712.6 | 1761.2 | 1580.0 |
| Comparative Example 3-4 | — | 1162.9 | 1502.6 | 1416.8 | 1566.8 | 1565.8 | 1509.8 | 1497.4 |

Dissolution Test Using 2nd Fluid for Disintegration Test Dissolved Amount (μg/ml)

TABLE 16

| Example No. | Coating ingredient | Elution time (min) | | | | | | |
|---|---|---|---|---|---|---|---|---|
| | | 1 | 3 | 10 | 30 | 60 | 180 | 360 |
| Example 3-1 | Citric acid 1/5 100 nm HAP | 6106.9 | 8806.8 | 9955.0 | 10655.3 | 10742.8 | 10784.9 | 10710.8 |
| Example 3-2 | SDS1/5 100 nm HAP | 1084.6 | 3248.8 | 4208.1 | 4902.0 | 4960.1 | 5020.2 | 4929.7 |

TABLE 16-continued

|  |  | Elution time (min) | | | | | | |
| --- | --- | --- | --- | --- | --- | --- | --- | --- |
| Example No. | Coating ingredient | 1 | 3 | 10 | 30 | 60 | 180 | 360 |
| Comparative Example 3-1 | 100 nm HAP | 1943.5 | 2409.8 | 2648.0 | 2658.9 | 2690.2 | 2657.9 | 2698.4 |
| Comparative Example 3-2 | Citric acid 1/5 | 1696.9 | 2761.1 | 1745.7 | 1787.6 | 1568.8 | 1592.7 | 1468.1 |
| Comparative Example 3-3 | SDS1/5 | 1161.5 | 1500.7 | 1775.2 | 1895.9 | 1818.2 | 1845.2 | 1809.2 |
| Comparative Example 3-4 | — | 1980.2 | 2286.6 | 2541.7 | 2600.9 | 2667.9 | 2509.7 | 2410.4 |

4. Trimethoprim
Dissolution Test Using Water Dissolved Amount (μg/ml)

TABLE 17

|  |  | Elution time (min) | | | | | | |
| --- | --- | --- | --- | --- | --- | --- | --- | --- |
| Example No. | Coating ingredient | 1 | 3 | 10 | 30 | 60 | 180 | 360 |
| Example 4-1 | Citric acid 1/5 100 nm HAP | 10546.6 | 11358.0 | 10853.1 | 10612.1 | 11559.5 | 10403.0 | 10144.4 |
| Comparative Example 4-1 | 100 nm HAP | 1085.3 | 1186.4 | 1208.2 | 1196.1 | 1209.9 | 1225.9 | 1212.6 |
| Comparative Example 4-2 | Citric acid 1/5 | 867.5 | 1036.6 | 756.3 | 812.1 | 907.9 | 750.2 | 806.9 |
| Comparative Example 4-3 | — | 354.6 | 531.0 | 685.0 | 677.9 | 671.8 | 672.0 | 656.3 |

Dissolution Test Using 2nd Fluid for Disintegration Test Dissolved Amount (μg/ml)

TABLE 18

|  |  | Elution time (min) | | | | | | |
| --- | --- | --- | --- | --- | --- | --- | --- | --- |
| Example No. | Coating ingredient | 1 | 3 | 10 | 30 | 60 | 180 | 360 |
| Example 4-1 | Citric acid 1/5 100 nm HAP | 10960.3 | 12969.8 | 13896.0 | 14411.1 | 13778.2 | 13081.5 | 13265.3 |
| Comparative Example 4-1 | 100 nm HAP | 2389.3 | 2532.8 | 2756.7 | 2698.8 | 2606.8 | 2532.8 | 2532.6 |
| Comparative Example 4-2 | Citric acid 1/5 | 1880.1 | 2192.6 | 2596.1 | 2264.9 | 2361.8 | 2600.2 | 1985.0 |
| Comparative Example 4-3 | — | 807.8 | 1160.4 | 1291.7 | 1344.0 | 1324.8 | 1296.5 | 1321.9 |

5. Probucol
Dissolution Test Using Water Dissolved Amount (μg/ml)

TABLE 19

|  |  | Elution time (min) | | | | | | |
| --- | --- | --- | --- | --- | --- | --- | --- | --- |
| Example No. | Coating ingredient | 1 | 3 | 10 | 30 | 60 | 180 | 360 |
| Example 5-1 | Disodium hydrogenphosphate 1/5 100 nm HAP | 88.9 | 115.1 | 339.7 | 550.8 | 462.5 | 649.3 | 561.5 |
| Comparative Example 5-1 | Disodium hydrogenphosphate 1/5 100 nm HAP | 223.1 | 211.3 | 244.8 | 254.8 | 257.8 | 277.7 | 289.1 |
| Comparative Example 5-2 | — | 0.7 | 2.7 | 3.7 | 6.1 | 7.6 | 8.3 | 9.7 |

Dissolution Test Using 2nd Fluid for Disintegration Test Dissolved Amount (μg/ml)

TABLE 20

| Example No. | Coating ingredient | Elution time (min) | | | | | | |
|---|---|---|---|---|---|---|---|---|
| | | 1 | 3 | 10 | 30 | 60 | 180 | 360 |
| Example 5-1 | Disodium hydrogenphosphate 1/5 100 nm HAP | 35.9 | 55.8 | 180.1 | 163.7 | 379.4 | 616.5 | 332.4 |
| Comparative Example 5-1 | Disodium hydrogenphosphate 1/5 100 nm HAP | 111.1 | 132.8 | 142.1 | 157.1 | 158.5 | 173.8 | 180.6 |
| Comparative Example 5-2 | — | 4.7 | 14.9 | 19.9 | 21.2 | 21.8 | 26.8 | 28.0 |

6. Sulpiride

Dissolution Test Using Water Dissolved Amount (μg/ml)

TABLE 21

| Example No. | Coating ingredient | Elution time (min) | | | | |
|---|---|---|---|---|---|---|
| | | 3 | 10 | 30 | 120 | 360 |
| Example 6-1 | Citric acid 1/100 100 nm HAP | 12877.9 | 12597.2 | 12425.1 | 12607.0 | 12814.7 |
| Example 6-2 | Citric acid 1/5 100 nm HAP | 29950.1 | 34620.2 | 34483.9 | 35514.1 | 35293.4 |
| Example 6-3 | Citric acid 3/1 100 nm HAP | 11590.8 | 10562.6 | 11248.7 | 11693.6 | 18186.7 |
| Example 6-4 | SDS1/100 100 nm HAP | 6970.6 | 6946.6 | 6985.9 | 6336.5 | 6695.6 |
| Example 6-5 | SDS1/5 100 nm HAP | 6494.7 | 6917.6 | 7185.6 | 6998.4 | 6923.0 |
| Example 6-6 | SDS3/1 100 nm HAP | 22841.0 | 22791.6 | 22667.0 | 22421.8 | 22631.4 |
| Comparative Example 6-1 | 100 nm HAP | 1146.0 | 1204.8 | 1084.8 | 1173.1 | 1144.8 |
| Comparative Example 6-2 | Citric acid 1/5 | 2028.2 | 1750.4 | 2069.3 | 2060.1 | 1733.0 |
| Comparative Example 6-3 | SDS1/5 | 2402.6 | 2416.2 | 2390.2 | 2421.4 | 2425.0 |
| Comparative Example 6-4 | — | 555.2 | 772.8 | 803.2 | 724.9 | 715.8 |

Dissolution Test Using 2nd Fluid for Disintegration Test Dissolved Amount (μg/ml)

TABLE 22

| Example No. | Coating ingredient | Elution time (min) | | | | |
|---|---|---|---|---|---|---|
| | | 3 | 10 | 30 | 120 | 360 |
| Example 6-1 | Citric acid 1/100 100 nm HAP | 18433.8 | 18076.0 | 19386.8 | 18655.3 | 18099.7 |
| Example 6-2 | Citric acid 1/5 100 nm HAP | 32715.2 | 35731.4 | 36896.7 | 38452.6 | 38081.1 |
| Example 6-3 | Citric acid 3/1 100 nm HAP | 19070.5 | 14546.7 | 11739.1 | 19157.5 | 23748.5 |
| Example 6-4 | SDS1/100 100 nm HAP | 9999.1 | 9821.7 | 9667.8 | 10128.6 | 9735.7 |
| Example 6-5 | SDS1/5 100 nm HAP | 9781.1 | 11062.0 | 13110.6 | 13485.1 | 13619.7 |
| Example 6-6 | SDS3/1 100 nm HAP | 23446.0 | 24541.4 | 25241.3 | 30004.4 | 27321.3 |
| Comparative Example 6-1 | 100 nm HAP | 5538.8 | 5098.0 | 5944.4 | 6170.0 | 6459.8 |
| Comparative Example 6-2 | Citric acid 1/5 | 5804.0 | 5445.8 | 5640.1 | 5523.4 | 5700.0 |
| Comparative Example 6-3 | SDS1/5 | 3203.0 | 3992.3 | 3928.0 | 3997.8 | 3746.2 |
| Comparative Example 6-4 | — | 5873.2 | 6995.7 | 6751.4 | 7206.2 | 6866.1 |

7. Lidocaine
Dissolution Test Using Water Dissolved Amount (μg/ml)

TABLE 23

| Example No. | Coating ingredient | Elution time (min) | | | | |
|---|---|---|---|---|---|---|
| | | 3 | 10 | 30 | 180 | 360 |
| Example 7-1 | Citric acid 1/5 100 nm HAP | 25916.0 | 28885.7 | 26856.3 | 27951.2 | 29934.4 |
| Comparative Example 7-1 | 100 nm HAP | 2545.8 | 2849.5 | 3764.3 | 4090.5 | 4528.8 |
| Comparative Example 7-2 | Citric acid 1/5 | 2253.5 | 2419.1 | 2850.8 | 3225.2 | 3582.6 |
| Comparative Example 7-3 | — | 1681.4 | 2204.3 | 2246.2 | 2919.3 | 3248.6 |

Dissolution Test Using 2nd Fluid for Disintegration Test Dissolved Amount (μg/ml)

TABLE 24

| Example No. | Coating ingredient | Elution time (min) | | | | |
|---|---|---|---|---|---|---|
| | | 3 | 10 | 30 | 180 | 360 |
| Example 7-1 | Citric acid 1/5 100 nm HAP | 25130.2 | 25237.1 | 26434.5 | 27018.1 | 35102.5 |
| Comparative Example 7-1 | 100 nm HAP | 8860.1 | 9028.3 | 8977.9 | 8765.0 | 8760.0 |
| Comparative Example 7-2 | Citric acid 1/5 | 2400.8 | 4230.3 | 5190.9 | 5566.3 | 6360.1 |
| Comparative Example 7-3 | — | 1873.3 | 2931.4 | 4039.8 | 5485.0 | 5469.0 |

8. Alacepril
Dissolution Test Using Water Dissolved Amount (μg/ml)

TABLE 25

| Example No. | Coating ingredient | Elution time (min) | | | | |
|---|---|---|---|---|---|---|
| | | 3 | 10 | 30 | 120 | 360 |
| Example 8-1 | Disodium hydrogenphosphate 1/5 100 nm HAP | 28634.4 | 23227.2 | 23692.2 | 24879.0 | 26119.0 |
| Example 8-2 | Disodium hydrogenphosphate 1/4 100 nm HAP | 34213.2 | 27170.9 | 28093.5 | 29257.2 | 31636.7 |
| Comparative Example 8-1 | — | 526.2 | 805.6 | 931.2 | 994.9 | 996.5 |

Dissolution Test Using 2nd Fluid for Disintegration Test Dissolved Amount (μg/ml)

TABLE 26

| Example No. | Coating ingredient | Elution time (min) | | | | |
|---|---|---|---|---|---|---|
| | | 3 | 10 | 30 | 120 | 360 |
| Example 8-1 | Disodium hydrogenphosphate 1/5 100 nm HAP | 26630.5 | 27702.2 | 30248.5 | 30328.3 | 27527.2 |
| Example 8-2 | Disodium hydrogenphosphate 1/4 100 nm HAP | 30525.2 | 30598.9 | 34879.5 | 34327.3 | 32384.9 |
| Comparative Example 8-1 | — | 2311.1 | 2514.7 | 2525.0 | 2588.4 | 2548.2 |

9. Erythromycin
Dissolution Test Using Water Dissolved Amount (μg/ml)

TABLE 27

| Example No. | Coating ingredient | Elution time (min) | | | | |
|---|---|---|---|---|---|---|
| | | 3 | 10 | 30 | 120 | 360 |
| Example 9-1 | Citric acid 1/5 100 nm HAP | 20911.5 | 22571.1 | 22154.7 | 23818.3 | 25648.9 |
| Comparative Example 9-1 | — | 635.0 | 861.6 | 944.7 | 927.7 | 846.1 |

Dissolution Test Using 2nd Fluid for Disintegration Test Dissolved Amount (μg/ml)

TABLE 28

| Example No. | Coating ingredient | Elution time (min) | | | | |
|---|---|---|---|---|---|---|
| | | 3 | 10 | 30 | 120 | 360 |
| Example 9-1 | Citric acid 1/5 100 nm HAP | 15564.0 | 16605.5 | 17082.5 | 18728.2 | 21844.7 |
| Comparative Example 9-1 | — | 2556.3 | 4984.2 | 5103.6 | 5904.1 | 6044.7 |

10. Haloperidol
Dissolution Test Using Water Dissolved Amount (μg/ml)

TABLE 29

| Example No. | Coating ingredient | Elution time (min) | | | | |
|---|---|---|---|---|---|---|
| | | 3 | 10 | 30 | 120 | 360 |
| Example 10-1 | Citric acid 1/5 100 nm HAP | 1000.9 | 814.7 | 560.4 | 592.4 | 562.7 |
| Comparative Example 10-1 | — | 8.2 | 10.0 | 11.3 | 12.8 | 13.1 |

Dissolution Test Using 2nd Fluid for Disintegration Test Dissolved Amount (μg/ml)

TABLE 30

| Example No. | Coating ingredient | Elution time (min) | | | | |
|---|---|---|---|---|---|---|
| | | 3 | 10 | 30 | 120 | 360 |
| Example 10-1 | Citric acid 1/5 100 nm HAP | 214.1 | 303.5 | 352.5 | 583.5 | 148.6 |
| Comparative Example 10-1 | — | 23.9 | 35.6 | 45.2 | 50.1 | 48.9 |

In addition, the pH of an aqueous solution after the passage of 60 minutes in each of the above described Examples, in which distilled water was used, is shown below.

The pH values of poorly-soluble substances and poorly-soluble substances coated with coating agents

TABLE 31

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 1-1 | Tolbutamide | 6.7 | 100 nm | 100 | Disodium hydrogenphosphate 1/10 | — |
| Example 1-2 | Tolbutamide | 6.8 | 100 nm | 100 | Disodium hydrogenphosphate 1/5 | — |
| Example 1-3 | Tolbutamide | 6.7 | 50 nm | 100 | Disodium hydrogenphosphate 1/5 | — |
| Example 1-4 | Tolbutamide | 6.9 | 100 nm | 100 | L-Arginine 1/5 | — |
| Example 1-5 | Tolbutamide | — | 100 nm | 100 | — | SDS 1/5 |
| Example 1-6 | Tolbutamide | — | 100 nm | 100 | Disodium | SDS 1/10 |
| Comparative Example 1-1 | Tolbutamide | 6.6 | 100 nm | 100 | hydrogenphosphate 1/10 | — |
| Comparative Example 1-2 | Tolbutamide | 6.4 | — | — | Disodium hydrogenphosphate 1/5 | — |

TABLE 31-continued

|  | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
| --- | --- | --- | --- | --- | --- | --- |
| Comparative Example 1-3 | Tolbutamide | 6.2 | — | — | L-Arginine 1/5 | — |
| Comparative Example 1-4 | Tolbutamide | — | — | — | — | SDS1/5 |
| Comparative Example 1-5 | Tolbutamide | 4.3 | — | — | — | — |

TABLE 32

|  | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
| --- | --- | --- | --- | --- | --- | --- |
| Example 2-1 | Bezafibrate | 6.3 | 100 nm | 100 | Disodium hydrogenphosphate 1/100 | — |
| Example 2-2 | Bezafibrate | 6.4 | 100 nm | 100 | Disodium hydrogenphosphate 1/10 | — |
| Example 2-3 | Bezafibrate | 6.2 | 10 μm | 100 | Disodium hydrogenphosphate 1/5 | — |
| Example 2-4 | Bezafibrate | 6.4 | 100 nm | 100 | Disodium hydrogenphosphate 1/5 | — |
| Example 2-5 | Bezafibrate | 6.4 | 100 nm | 50 | Disodium hydrogenphosphate 1/5 | — |
| Example 2-6 | Bezafibrate | 6.2 | 100 nm | 10 | Disodium hydrogenphosphate 1/5 | — |
| Example 2-7 | Bezafibrate | 6.4 | 50 nm | 100 | Disodium hydrogenphosphate 1/5 | — |
| Example 2-8 | Bezafibrate | 7.8 | 100 nm | 100 | Disodium hydrogenphosphate 3/1 | — |
| Example 2-9 | Bezafibrate | 6.7 | 100 nm | 10 | L-Arginine 1/5 | — |
| Example 2-10 | Bezafibrate | 7.1 | 100 nm | 100 | Sodium hydrogencarbonate 1/5 | — |
| Example 2-11 | Bezafibrate | — | 100 nm | 100 | — | SDS1/5 |
| Comparative Example 2-1 | Bezafibrate | 6.0 | 100 nm | 100 | — | — |
| Comparative Example 2-2 | Bezafibrate | 5.8 | 100 nm Mixing | 100 | — | — |
| Comparative Example 2-3 | Bezafibrate | 6.2 | — | — | Disodium hydrogenphosphate 1/5 | — |
| Comparative Example 2-4 | Bezafibrate | 6.5 | — | — | Sodium hydrogencarbonate 1/5 | — |
| Comparative Example 2-5 | Bezafibrate | — | — | — | — | SDS1/5 |
| Comparative Example 2-6 | Bezafibrate | 4.3 | — | — | — | — |

TABLE 33

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 3-1 | Famotidine | 6.3 | 100 nm | 100 | Citric acid 1/5 | — |
| Example 3-2 | Famotidine | — | 100 nm | 100 | — | SDS1/5 |
| Comparative Example 3-1 | Famotidine | 9.3 | 100 nm | 100 | — | — |
| Comparative Example 3-2 | Famotidine | 5.5 | — | — | Citric acid 1/5 | — |
| Comparative Example 3-3 | Famotidine | — | — | — | — | SDS1/5 |
| Comparative Example 3-4 | Famotidine | 8.4 | — | — | — | — |

TABLE 34

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 4-1 | Trimethoprim | 6.3 | 100 nm | 100 | Citric acid 1/5 | — |
| Comparative Example 4-1 | Trimethoprim | 9.1 | 100 nm | 100 | — | — |
| Comparative Example 4-2 | Trimethoprim | 5.9 | — | — | Citric acid 1/5 | — |
| Comparative Example 4-3 | Trimethoprim | 8.4 | — | — | — | — |

TABLE 35

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 5-1 | Probucol | 9.1 | 100 nm | 100 | Disodium hydrogenphosphate 1/5 | — |
| Comparative Example 5-1 | Probucol | 9.2 | 100 nm | 100 | Disodium hydrogenphosphate 1/5 | — |
| Comparative Example 5-2 | Probucol | 5.4 | — | — | — | — |

TABLE 36

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 6-1 | Sulpiride | 8.9 | 100 nm | 100 | Citric acid 1/100 | — |
| Example 6-2 | Sulpiride | 7.1 | 100 nm | 100 | Citric acid 1/5 | — |
| Example 6-3 | Sulpiride | 6.2 | 100 nm | 100 | Citric acid 3/1 | — |
| Example 6-4 | Sulpiride | — | 100 nm | 100 | — | SDS1/100 |
| Example 6-5 | Sulpiride | — | 100 nm | 100 | — | SDS1/5 |
| Example 6-6 | Sulpiride | — | 100 nm | 100 | — | SDS3/1 |
| Comparative Example 6-1 | Sulpiride | 9.5 | 100 nm | 100 | — | — |
| Comparative Example 6-2 | Sulpiride | 6.6 | — | — | Citric acid 1/5 | — |
| Comparative Example 6-3 | Sulpiride | — | — | — | — | SDS1/5 |
| Comparative Example 6-4 | Sulpiride | 9.3 | — | — | — | — |

TABLE 37

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 7-1 | Lidocaine | 7.4 | 100 nm | 100 | Citric acid 1/5 | — |
| Comparative Example 7-1 | Lidocaine | 9.8 | 100 nm | 100 | — | — |
| Comparative Example 7-2 | Lidocaine | 6.8 | — | — | Citric acid 1/5 | — |
| Comparative Example 7-3 | Lidocaine | 9.7 | — | — | — | — |

TABLE 38

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 8-1 | Alacepril | 5.9 | 100 nm | 100 | Disodium hydrogenphosphate 1/5 | — |
| Example 8-2 | Alacepril | 6.2 | 100 nm | 100 | Disodium hydrogenphosphate 1/4 | — |
| Comparative Example 8-1 | Alacepril | 2.9 | — | — | — | — |

TABLE 39

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 9-1 | Erythromycin | 6.2 | 100 ml | 100 | Citric acid 1/5 | — |
| Comparative Example 9-1 | Erythromycin | 9.6 | — | — | — | — |

TABLE 40

| | Poorly-soluble substance | pH at 60 minutes after dissolution | Particle diameter of HAP (μm) | Coating rate by HAP (%) | pH adjustor ratio to poorly-soluble substance | Surfactant ratio to poorly-soluble substance |
|---|---|---|---|---|---|---|
| Example 10-1 | Haloperidol | 5.6 | 100 nm | 100 | Citric acid 1/5 | — |
| Comparative Example 10-1 | Haloperidol | 8.1 | — | — | — | — |

Industrial Applicability

The substance with improved aqueous solubility produced by the present invention can be used for pharmaceutical products, veterinary pharmaceutical products, quasi-drugs, cosmetic products, food products, agricultural chemicals, and the like.

The invention claimed is:

1. A method of making a coated substance comprising:
providing an active substance with poor water solubility;
providing hydroxyapatite microparticles;
providing microparticles of a pH adjuster or surfactant as a powder with a particle diameter of 150 μm or less;
applying mechanical energy to a combination of said active substance and said hydroxyapatite microparticles to form a recovered substance;
applying mechanical energy to a combination of said recovered substance and said microparticles of a pH adjuster or surfactant to produce a coated substance,
wherein the microparticles of the pH adjuster or surfactant are present in an amount of 1/100 to 3 times the amount of the poorly soluble substance; and
wherein the coated substance has improved water solubility as compared with the poorly water soluble substance by itself.

2. The method of claim 1, wherein the amount of the surfactant used is 1% to 300% by mass with respect to the poorly water soluble substance.

3. The method of claim 1, wherein the method of applying mechanical energy to the combination of said active substance and said hydroxyapatite microparticles to form a recovered substance is a method involving mechanical fusion.

4. The method of claim 1, wherein the method of applying mechanical energy to the combination of said active substance and said hydroxyapatite microparticles to form a recovered substance is a method involving hybridization.

5. The method of claim 1, wherein the mean particle diameter of the hydroxyapatite microparticles is 100 μm or less.

6. The method of claim 5, wherein the mean particle diameter of the calcium compound microparticles is 50 to 200 nm.

7. The method of claim 1, wherein the pH adjuster is selected from the group consisting of disodium hydrogen phosphate, L-arginine, sodium hydrogen carbonate, citric acid, and sodium dihydrogen phosphate.

8. The method of claim 1, wherein the surfactant is sodium dodecyl sulfate.

9. The method of claim 1, wherein the poorly water soluble substance is selected from the group consisting of a pharmaceutical active agent, a veterinary pharmaceutical a cosmetic, an agricultural chemical, and a food additive.

10. A method of claim 1, wherein the poorly water soluble substance is selected from the group consisting of tolbutamide, bezafibrate, famotidine, trimethoprim, probucol, sulpiride, lidocaine, alacepril, erythromycin, and haloperidol.

11. The method of claim 1, wherein the method of applying mechanical energy to the combination of said recovered substance and said microparticles of a pH adjuster or surfactant to produce a coated substance is a method involving hybridization.

12. The method of claim 1, wherein the method of applying mechanical energy to the combination of said recovered substance and said microparticles of a pH adjuster or surfactant to produce a coated substance is a method involving mechanical fusion.

13. The method of claim 1, wherein the method of applying mechanical energy to the combination of said recovered substance and said microparticles of a pH adjuster or surfactant to produce a coated substance is a method involving mechanical fusion or hybridization.

14. The method of claim 1, wherein the method of applying mechanical energy to the combination of said active substance and said hydroxyapatite microparticles to form a recovered substance is a method involving mechanical fusion or hybridization.

* * * * *